United States Patent
Kuo et al.

(10) Patent No.: US 7,205,298 B2
(45) Date of Patent: Apr. 17, 2007

(54) SUBSTITUTED TRIAZINE KINASE INHIBITORS

(75) Inventors: Gee-Hong Kuo, Scotch Plains, NJ (US); Alan DeAngelis, Pennington, NJ (US); Aihua Wang, Jamison, PA (US); Yan Zhang, Spingfield, NJ (US); Stuart L. Emanuel, Doylestown, PA (US); Steve Middleton, Flemington, NJ (US)

(73) Assignee: Janssen Pharmaceutica N.V. (BE)

( * ) Notice: Subject to any disclaimer, the term of this patent is extended or adjusted under 35 U.S.C. 154(b) by 179 days.

(21) Appl. No.: 10/622,721

(22) Filed: Jul. 18, 2003

(65) Prior Publication Data

US 2004/0082581 A1    Apr. 29, 2004

Related U.S. Application Data

(60) Provisional application No. 60/396,948, filed on Jul. 18, 2002.

(51) Int. Cl.
| | |
|---|---|
| C07D 251/42 | (2006.01) |
| C07D 251/48 | (2006.01) |
| C07D 241/10 | (2006.01) |
| C07D 401/04 | (2006.01) |
| C07D 403/04 | (2006.01) |
| A61K 31/53 | (2006.01) |
| A61K 31/497 | (2006.01) |
| A61K 31/4427 | (2006.01) |
| A61P 35/00 | (2006.01) |
| A61P 19/02 | (2006.01) |

(52) U.S. Cl. ............... 514/245; 544/206; 544/207; 544/218

(58) Field of Classification Search ............ 544/206, 544/207, 208, 218; 514/241, 245
See application file for complete search history.

(56) References Cited

U.S. PATENT DOCUMENTS

2002/0016825 A1    2/2002    Falotico et al.

FOREIGN PATENT DOCUMENTS

| WO | WO 96/32907 | 10/1996 |
|---|---|---|
| WO | WO 01/25220 A1 | 4/2001 |

OTHER PUBLICATIONS

Cecil Textbook of Medicine, edited by Bennet, J.C., and Plum F., 20th edition, vol. 1, 1004-1010, 1996.*
Shapiro, Clinical Cancer Research 10: 4270-4275, 2004.*
Davis et al., "Prevention of Chemotherapy-induced Alopecia in Rats by CDK Inhibitors", Science, vol. 291, pp. 134-137 (2001).
International Search Report dated Dec. 5, 2003 for related International Application No. PCT/US03/22390.

* cited by examiner

Primary Examiner—Venkataraman Balasubramanian
(74) Attorney, Agent, or Firm—Laura Donnelly

(57) ABSTRACT

The present invention provides substituted 1,3,5-triazine compounds as kinase inhibitors and a method for treating or ameliorating a kinase mediated disorder.

10 Claims, No Drawings

SUBSTITUTED TRIAZINE KINASE INHIBITORS

FIELD OF THE INVENTION

The present invention claims priority from U.S. Provisional Application 60/396,948 filed Jul. 18, 2002, entitled "Substituted Triazine Kinase Inhibitors" the contents of which are hereby incorporated by reference. The present invention provides substituted triazine compounds as kinase inhibitors and a method for use thereof. More particularly, the present invention provides substituted 1,3,5-triazine compounds as kinase inhibitors and a method for treating or ameliorating a kinase mediated disorder.

BACKGROUND OF THE INVENTION

The cell division cycle is one of the most fundamental processes in biology which ensures the controlled proliferation of cells in multicellular organisms. Under normal growth conditions, cell proliferation is tightly regulated in response to diverse intracellular and extracellular signals. This is achieved by a complex network of proto-oncogenes and tumor-suppressor genes that are components of various signal transduction pathways. Activation of a proto-oncogene and/or a loss of a minor suppressor gene can lead to the unregulated activity of the cell cycle machinery. This, in turn, will lead to unregulated cell proliferation and to the accumulation of genetic errors which ultimately result in the development of cancer (Pardee, A. B., *Science*, 1989, 246: 603–608). In the eukaryotic cell cycle a key role is played by the cyclin dependent kinases. CDK complexes are formed via the association of a regulatory cyclin subunit and a catalytic kinase subunit. In mammalian cells, the combination of the kinase subunits (such as CDK1, CDK2, CDK4 or CDK6) with a variety of cyclin subunits (such as cyclin A, B, D1, D2, D3 or E) results in the assembly of functionally distinct kinase complexes. The coordinated activation of these complexes drives the cells through the cell cycle and ensures the fidelity of the process (Draetta, G., *Trends Biochem. Sci.,* 1990, 15:378–382; Sherr, C. J., *Cell,* 1993, 73:1059–1065). Each step in the cell cycle is regulated by a distinct and specific cyclin-dependent kinase. Regulation occurs at the boundaries of the G1/S and G2/M phases, two major transition points of the cell cycle. For example, complexes of CDK4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the CDK1/cyclin B complex controls the entry into M-phase (Sherr, 1993). A key regulator of these transitions is CDK1 kinase, a universal intracellular factor which triggers the G2/M transition of the cell cycle in all organisms. Both biochemical and genetic evidence have shown that CDK1 is the primary activity required for a cell to enter mitosis in all eukaryotic cells. In late G2, it is present as an inactive complex of CDK1 and cyclin B. In M phase, it is activated and thereafter displays kinase activity. CDK1 is known to phosphorylate a number of proteins including histone H1, DNA polymerase alpha, RNA polymerase II, retinoblastoma tumor suppressor protein (RB), p53, nucleolin, cAbl and lamin A. The kinase activity of CDK1 is required for entry of cells into mitosis, i.e., for passage from the G2 phase of the cell cycle into the M phase (Lee M. and Nurse P., *Trends Genet.,* 1988, 4:289–90; Dunphy W. G., Brizuela L., Beach D. and Newport J., *Cell,* 1988, 54:423–431; Gautier J., Norbury C., Lohka M., Nurse P. and Maller J., *Cell,* 1988, 54:433–439; Cross F., Roberts J. and Weintraub H., *Ann. Rev. Cell Biol.,* 1989, 5:341–395; Hunt, T. and Sherr, C., *Curr. Opinion Cell Biol.,* 1989, 1:268–274; and, Nurse, P., *Nature,* 1990, 344:503–508). Therefore, using cyclin dependent kinase inhibitors for tumor therapy is believed to inhibit tumor growth or controlling unregulated cell proliferation. Patent application WO 01/25220 describes a series of triazines that bind to ATP or GTP and/or catalyze phosphoryl transfer.

SUMMARY OF THE INVENTION

The present invention provides a compound of Formula (I):

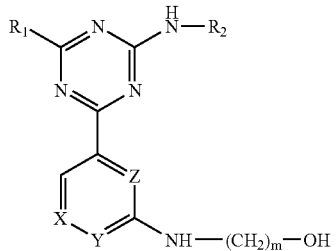

Formula (I)

wherein
X, Y and Z are independently selected from the group consisting of CH and N; wherein m is an integer from 2 to 5; wherein X, Y and Z include at least one CH atom and at least one N atom; and, wherein a N atom may simultaneously occupy only the X and Z positions;
$R_1$ is selected from the group consisting of hydrogen and $NH_2$; and,
$R_2$ is selected from the group consisting of phenyl (wherein phenyl is substituted with one substituent selected from the group consisting of a halogen and a heterocyclyl) and 1,4-benzodioxinyl;
and pharmaceutically acceptable salts thereof.

An aspect of the present invention is a method for treating or ameliorating a kinase mediated disorder in a subject in need thereof comprising administering to the subject a therapeutically effective amount of a compound of Formula (I).

Another aspect of the present invention includes a method for treating or ameliorating a cyclin dependent kinase (CDK), a glycogen synthase kinase (GSK), a vascular endothelial growth factor receptor kinase (VEGF-R) or a human epidermal growth factor receptor-2 (HER-2) kinase mediated disorder. The terms "cyclin dependent kinase" and "glycogen synthase kinase" additionally include the subtypes of these enzymes as well.

A further aspect of the present invention includes a method for producing the instant compounds and pharmaceutical compositions and medicaments thereof.

DETAILED DESCRIPTION OF THE INVENTION

An aspect of the present invention includes compounds of Formula (I) wherein, X, Y and Z are independently selected from the group consisting of CH and N; wherein m is 3; wherein X, Y and Z are dependently selected from at least one CH atom and at least one N atom; wherein a N atom may simultaneously occupy only the X and Z positions; wherein the heteroaryl ring thus formed is selected from the group consisting of pyridinyl and pyrazinyl; wherein pyridinyl is attached to the triazine ring at the 3 or 4 position of the pyridine ring; and, wherein pyrazinyl is attached to the triazine ring at the 6 position of the pyrazine ring.

Another aspect of the present invention includes compounds of Formula (I) wherein $R_2$ is selected from the group consisting of phenyl (wherein phenyl is substituted with one substituent selected from the group consisting of chlorine and 4-morpholinyl) and 1,4-benzodioxinyl.

Exemplified compounds of the present invention include a compound of Formula (Ia):

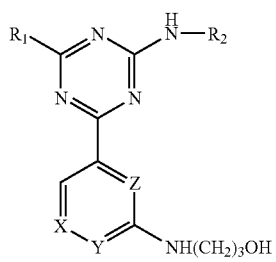

Formula (Ia)

wherein X, Y, Z, $R_1$ and $R_2$ are dependently selected according to the table provided below:

| Cpd | X  | Y  | Z  | $R_1$ | $R_2$ |
|-----|----|----|----|-------|-------|
| 1   | N  | CH | CH | H     | 3-Cl-Ph; |
| 2   | CH | N  | CH | H     | 3-Cl-Ph; |
| 3   | N  | CH | N  | H     | 3-Cl-Ph; |
| 4   | CH | N  | CH | $NH_2$ | 3-Cl-Ph; |
| 5   | N  | CH | CH | H     | 2,3-dihydro-1,4-benzodioxin-6-yl; or |
| 6   | N  | CH | CH | H     | 4-(4-morpholinyl)Ph. |

The compounds of the present invention may also be present in the form of pharmaceutically acceptable salts. For use in medicine, the salts of the compounds of this invention refer to non-toxic "pharmaceutically acceptable salts" (Ref. *International J. Pharm.*, 1986, 33, 201–217; *J. Pharm. Sci.*, 1997 (January), 66, 1, 1). Other salts may, however, be useful in the preparation of compounds according to this invention or of their pharmaceutically acceptable salts. Representative organic or inorganic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The present invention includes within its scope prodrugs of the compounds of this invention. In general, such prodrugs are considered to be functional derivatives of the compounds for purposes of this disclosure and these prodrugs are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in *"Design of Prodrugs"*, ed. H. Bundgaard, Elsevier, 1985.

Unless specified otherwise, the term "alkyl" refers to a saturated straight or branched chain wherein the chain consists solely of 1–8 hydrogen substituted carbon atoms, 1–6 hydrogen substituted carbon atoms or 1–4 hydrogen substituted carbon atoms.

The term "heterocyclyl" refers to a saturated or partially unsaturated ring having five members of which at least one member is a N, O or S atom and which optionally contains one additional O atom or one, two or three additional N atoms; a saturated or partially unsaturated ring having six members of which one, two or three members are a N atom; a saturated or partially unsaturated bicyclic ring having nine members of which at least one member is a N, O or S atom and which optionally contains one, two or three additional N atoms; or, a saturated or partially unsaturated bicyclic ring having ten members of which one, two or three members are a N atom. Examples include, and are not limited to, pyrrolinyl, pyrrolidinyl, dioxolanyl, imidazolinyl, imidazolidinyl, pyrazolinyl, pyrazolidinyl, piperidinyl, morpholinyl or piperazinyl.

The term "heteroaryl" refers to an aromatic monocyclic ring system containing five members of which at least one member is a N, O or S atom and which optionally contains one, two or three additional N atoms; an aromatic monocyclic ring having six members of which one, two or three members are a N atom; an aromatic bicyclic ring having nine members of which at least one member is a N, O or S atom and which optionally contains one, two or three additional N atoms; or, an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, quinolinyl or isoquinolinyl.

The term "halo" or "halogen" refers to a fluoro, chloro, bromo or iodo atom.

"Independently" means that when a group is substituted with more than one substituent and that the substituents may be the same or different. "Dependently" means that the substituents are specified in an indicated combination of structure variables.

An aspect of the invention is a composition or medicament comprising a pharmaceutically appropriate carrier and any of the compounds of the present invention. Illustrative of the invention is a composition or medicament made by mixing an instant compound and a pharmaceutically appropriate carrier. Another illustration of the invention is a process for making a composition or medicament comprising mixing any of the compounds described above and a pharmaceutically appropriate carrier. Further illustrative of the present invention are compositions or medicaments comprising one or more compounds of this invention in association with a pharmaceutically appropriate carrier.

As used herein, the term "composition" is intended to encompass a product comprising the specified ingredients in the specified amounts, as well as any product which results, directly or indirectly, from combinations of the specified ingredients in the specified amounts for treating or ameliorating a kinase mediated disorder or for use as a medicament.

The compounds of the present invention are kinase inhibitors useful in a method for treating or ameliorating a kinase mediated disorder. In an aspect of the invention, the kinase is selected from a cyclin dependent kinase or subtype thereof, a glycogen synthase kinase or subtype thereof, a vascular endothelial growth factor receptor kinase or a human epidermal growth factor receptor-2 kinase. The instant compounds are useful in the inhibition of a number of proteins having kinase activity. The cyclin dependent kinase and glycogen synthase kinase as used in this invention are terms that refer to a plurality of enzymes that each have similar enzyme substrate specificities or similar active sites within the enzymatic molecule. Thus, the enzymes encompass all of their subtypes, i.e., those other molecules having similar enzyme substrate specificities or similar active sites within the enzymatic molecule.

In another aspect of the invention, the kinase is selected from a cyclin dependent kinase or subtype thereof, a glycogen synthase kinase or subtype thereof or a vascular endothelial growth factor receptor kinase. In a further aspect of the invention, the cyclin dependent kinase subtype is selected from cyclin dependent kinase-1 or cyclin dependent kinase-2.

While the molecules of this invention are useful for inhibiting cell proliferation, particularly for inhibiting tumor cell proliferation, the molecules of this invention may limit chemotherapy-induced alopecia. Many conventional cytotoxic cancer therapies destroy the rapidly dividing epithelium of the hair follicle and induce alopecia (hair loss). Inhibition of cyclin dependent kinases during conventional chemotherapy may represent a therapeutic strategy for the prevention of chemotherapy-induced alopecia by arresting the cell cycle and reducing the sensitivity of epithelial cells to antitumor agents (Davis S. T., et al., Prevention of chemotherapy-induced alopecia in rats by CDK inhibitors, Science, 2001, (January 5), 291, 5501, 25–6). Accordingly, to be useful in a method for the prevention of chemotherapy-induced alopecia, a preferred cyclin dependent kinase inhibitor is cytostatic rather than cytotoxic and preferably is able to hold the cell in a stationary growth phase, thus protecting a hair follicle from the cytotoxic activity of a conventional chemotherapeutic agent being administered at the same time. In this way, topical application of non-apoptotic CDK inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration and proliferation is largely responsible for restenosis following angioplasty (Ross, R., Nature, 1993, 362, 801–809). Recent studies have shown that CDK2 is activated very early after endothelial denudation in a rat carotid artery model of restenosis (Wei, G. L., et al., Circ. Res., 1997, 80, 418–426). Therefore, antiproliferative therapies targeted to cyclin dependent kinases or other components of the cell cycle machinery are thought to be a suitable approach to treat these disorders. One aspect for use of the compounds of the present invention is a method for the treatment or amelioration of restenosis wherein a CDK inhibitor is impregnated on the surface of an angioplasty balloon or stent. Drug delivery is thus targeted to the local environment where endothelial and smooth muscle cell proliferation are the leading cause of vascular occlusion following angioplasty and resulting restenosis in the area of a stent's implantation (Eric E. Brooks, et al., CVT-313, a Specific and Potent Inhibitor of CDK2 That Prevents Neointimal Proliferation, J. Biol. Chem., 1997, 272(46):29207–29211).

For the purposes of this invention, a kinase mediated disorder includes a disorder wherein aberrant cyclin dependent kinase (CDK) activity, vascular endothelial growth factor (VEGF-R) kinase activity, human epidermal growth factor receptor-2 (HER-2) kinase activity or glycogen synthase kinase (GSK) activity results in uncontrolled or unregulated cell proliferation of neoplastic, tumorigenic or nonneoplastic cells resulting in tumor growth or cancer, abherrant cell growth, alopecia, restenosis, vascular occlusion, retinopathy, and the like.

Thus, in an aspect of the present invention, the invention includes a prophylactic as well as a therapeutic method for treating or ameliorating a kinase mediated disorder in a subject in need thereof comprising administering to the subject a therapeutically effective amount of a compound of Formula (I) (supra) or composition thereof.

In an aspect of the invention, the kinase is selected from a CDK or subtype thereof, a GSK or subtype thereof, a VEGF-R kinase or a HER-2 kinase. In another aspect of the invention, the kinase is selected from a CDK or subtype thereof, a GSK or subtype thereof or a VEGF-R kinase. In a further aspect of the invention, the CDK subtype is selected from CDK-1 or CDK-2. The therapeutically effective amount of the compounds of Formula (I) exemplified in such a method is preferably from about 0.001 mg/kg/day to about 300 mg/kg/day.

The term "prophylactic" refers to a method for preventing a kinase mediated disorder in a subject in need thereof comprising administering to the subject prophylactically effective amount of a compound of Formula (I) or a composition thereof.

Another aspect of the present invention includes the use of a compound of Formula (I) for the preparation of a medicament for preventing, treating or ameliorating a kinase mediated disorder in a subject in need thereof.

In a still further aspect, the invention relates to a method for inhibiting growth of a cell comprising administering to the cell a growth inhibiting amount of a compound of Formula (I). In one embodiment the cell is in need of growth regulation and in another embodiment the cell is a transformed cell or a cancer cell.

In accordance with the methods of the present invention, an individual compound of the present invention or a composition thereof can be administered separately, at different times during the course of therapy or concurrently in divided or single combination forms. Where prophylactic administration is desired, administration can occur prior to the manifestation of symptoms characteristic of a kinase associated disease or disorder such that the disease or disorder is prevented or, alternatively, delayed in its progression. The instant invention is therefore to be understood as embracing all such regimes of simultaneous or alternating treatment and the term "administering" is to be interpreted accordingly.

The term "subject" as used herein, refers to an animal, preferably a mammal, most preferably a human, who has been the object of treatment, observation or experiment and is at risk of (or susceptible to) developing a disease of disorder or having a disease of disorder related to unregulated CDK, GSK, VEGF-R or HER-2 activity.

The term "therapeutically effective amount" or "effective amount," as used herein, means that amount of active compound or pharmaceutical agent that elicits the biological or medicinal response (such as inhibiting activation of a CDK or subtype thereof, a GSK or subtype thereof, a VEGF-R kinase or a HER-2 kinase) in a tissue system, animal or human, that is being sought by a researcher, veterinarian, medical doctor, or other clinician, which includes alleviation of the symptoms of the disease or disorder being treated.

Selective protein kinase inhibitors are highly desirable given the ubiquitous nature of protein kinases and their important roles in various signal transduction pathways. Often, overactivity of a given protein kinase will result in a certain set of disorders and diseases. Therefore, inhibitory compounds that are selective to a particular family of protein kinases, a single kinase or a certain isoform of a kinase relative to other kinases are superior therapeutic agents. Such compounds should demonstrate greater efficacy and lower toxicity by virtue of their specificity. Accordingly, it will be appreciated by one skilled in the art that a compound of Formula (I) is therapeutically effective for treating or ameliorating certain kinase or multiple kinase mediated disorders associated with the overactivity of one or more kinases; wherein the kinase is selected from a CDK or subtype thereof, a GSK or subtype thereof, a VEGF-R kinase or a HER-2 kinase by inhibiting the kinase activity. The usefulness of a compound of Formula (I) as a kinase inhibitor can be determined according to the methods disclosed herein and the scope of such usefulness includes use in one or more kinase mediated disorders.

Therefore, the term "kinase mediated disorder" as used herein, includes, and is not limited to disorders and diseases associated with kinase overactivity and conditions that accompany such diseases, wherein kinase overactivity includes unregulated cellular mitosis, unregulated cell proliferation and upregulated kinase activity. Disorders and diseases associated with unregulated cell proliferation include cancers (such as glioma cancers, lung cancers, breast cancers, colorectal cancers, prostate cancers, gastric cancers, esophageal cancers, leukemias and lymphomas), and associated pathologies such as abnormal cell proliferation, benign or neoplastic tumor growth, tumor vascularization, as well as angiopathy, angiogenesis, and chemotherapy-induced alopecia. Disorders and diseases associated with unregulated cellular mitosis, unregulated cell proliferation and upregulated cyclin dependent kinase activity include atherosclerosis, transplantation-induced vasculopathies, neointima formation, lung fibrosis, pulmonary fibrosis, glomerulonephritis, glomerulosclerosis, congenital multicystic renal dysplasia, kidney fibrosis, diabetic retinopathy, rheumatoid arthritis and restenosis.

The term "upregulated cyclin dependent kinase activity" refers to either:
1. CDK expression in cells which normally do not express CDK,
2. CDK expression by cells which normally do not express CDK,
3. increased CDK expression leading to unwanted cell proliferation, or
4. mutations leading to constitutive activation of CDK.

The existence of an inappropriate or abnormal level or activity of CDK is determined by procedures well known in the art and include radioimmunoassays, ELISAs or the same or a variation of the enzymatic assays provided infra.

The term "disorders and diseases associated with unregulated cell proliferation" refers to disorders wherein unwanted cell proliferation of one or more subset of cells in a multicellular organism occurs resulting in harm (such as discomfort or decreased life expectancy) to the multicellular organism. Such cell proliferative disorders can occur in different types of animals and humans and include, but are not limited to, cancers (glioma, lung, breast, colorectal, prostate, gastric and esophageal, leukemias and lymphomas), atherosclerosis, restenosis, psoriasis, papilloma, pulmonary fibrosis, in-stent stenosis, vascular graft restinosis, glomerular nephritis, diabetic retinopathy and rheumatoid arthritis.

Another aspect of the present invention includes a method for inhibiting a cell's unregulated entry into mitosis comprising administering to the cell an effective amount of a compound of Formula (I) or composition thereof for selectively inhibiting kinase activity in the cell. As used herein the term "selectively" means, for example, that the compound in question is capable of inhibiting, for example, one or more cyclin dependent kinase activities but does not substantially inhibit another kinase such as a VEGF-R kinase or the like.

Another aspect of the present invention includes a method for inhibiting unregulated cell proliferation in a tumor comprising administering to the tumor an effective amount of a compound of Formula (I) or composition thereof for selectively inhibiting kinase activity in the tumor.

Another aspect of the present invention includes a method for down-regulating cyclin dependent kinase activity in a cell comprising administering to the cell an effective amount of a compound of Formula (I) or composition thereof for selectively down-regulating cyclin dependent kinase activity in the cell.

Another aspect of the present invention includes a method for treating or ameliorating chemotherapy induced alopecia in a subject in need thereof comprising topically administering to the subject a therapeutically effective amount of a compound of Formula (I) or composition thereof.

Another aspect of the present invention includes a method for use of a compound of Formula (I) or composition thereof advantageously administered in one or more cell anti-proliferation therapies including chemotherapy, radiation therapy, gene therapy or immunotherapy for preventing, treating or ameliorating a kinase mediated disorder. The combination therapy can include:
1. co-administration of a compound of Formula (I) or composition thereof and a chemotherapeutic agent for preventing, treating or ameliorating a kinase mediated disorder,
2. sequential administration of a compound of Formula (I) or composition thereof and a chemotherapeutic agent for preventing, treating or ameliorating a kinase mediated disorder,
3. administration of a composition containing a compound of Formula (I) and a chemotherapeutic agent for preventing, treating or ameliorating a kinase mediated disorder, or,
4. simultaneous administration of a separate composition containing a compound of Formula (I) and a separate composition containing a chemotherapeutic agent for preventing, treating or ameliorating a kinase mediated disorder.

For example, the compounds of this invention have been demonstrated to be useful in combination therapies with at least one other chemotherapeutic agent for the treatment of a number of different cancers and advantageously appear to facilitate the use of a reduced dose of the chemotherapeutic agent that is recommended for a particular cancer or cell proliferation disorder. Therefore, it is contemplated that the compounds of this invention can be used in a treatment regime before the administration of a particular chemotherapeutic agent recommended for the treatment of a particular cancer, during administration of the chemotherapeutic agent or after treatment with a particular chemotherapeutic agent.

The term "chemotherapeutic agents" includes, and is not limited to, anti-angiogenic agents, anti-tumor agents, cytotoxic agents, inhibitors of cell proliferation, and the like. The term "treating or ameliorating" includes, and is not limited to, facilitating the eradication of, inhibiting the progression of or promoting stasis of a malignancy. For example, an inhibitor compound of the present invention, acting as an anti-angiogenic agent can be administered in a dosing regimen with at least one other cytotoxic compound, such as a DNA alkylating agent.

Preferred anti-tumor agents are selected from the group consisting of cladribine (2-chloro-2'-deoxy-(beta)-D-adenosine), chlorambucil (4-(bis(2-chlorethyl)amino)benzenebutanoic acid), DTIC-Dome (5-(3,3-dimethyl-1-triazeno)-imidazole-4-carboxamide), platinum chemotherapeutics and nonplatinum chemotherapeutics. Platinum containing anti-tumor agents include, but are not limited to, cisplatin (CDDP) (cis-dichlorodiamineplatinum). Non-platinum containing anti-tumor agents include, but are not limited to, adriamycin (doxorubicin), aminopterin, bleomycin, camptothecin, carminomycin, combretastatin(s), cyclophosphamide, cytosine arabinoside, dactinomycin, daunomycin, epirubicin, etoposide (VP-16), 5-fluorouracil (5FU), herceptin actinomycin-D, methotrexate, mitomycin C, tamoxifen, taxol, taxotere, thiotepa, vinblastine, vincristine, vinorelbine and derivatives and prodrugs thereof. Each anti-tumor agent is administered in a therapeutically effective amount, which varies based on the agent used, the type of malignancy to be treated or ameliorated and other conditions according to methods well known in the art.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating agents are used widely to treat cancer. The efficacious dose of cisplatin used in clinical applications is about 20 mg/m$^2$ for 5 days every three weeks for a total of three courses. Cisplatin is not absorbed orally and must therefore be delivered via injection intravenously, subcutaneously, intratumorally or intraperitoneally. Further useful agents include compounds that interfere with DNA replication, mitosis and chromosomal segregation. Such chemotherapeutic agents include adriamycin (doxorubicin), etoposide, verapamil or podophyllotoxin and the like and are widely used in clinical settings for tumor treatment. These compounds are administered through bolus injections intravenously at doses ranging from about 25 to about 75 mg/m$^2$ at 21 day intervals (for adriamycin) or from about 35 to about 50 mg/m$^2$ (for etoposide) intravenously or at double the intravenous dose orally. Agents that disrupt the synthesis and fidelity of polynucleotide precursors such as 5-fluorouracil (5-FU) are preferentially used to target tumors. Although quite toxic, 5-FU is commonly used via intravenous administration with doses ranging from about 3 to about 15 mg/kg/day.

Another aspect of the present invention includes a method for administering a compound of the present invention in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

Another aspect of the present invention includes a method for administering a compound of the present invention in combination with a gene therapy. As used herein, "gene therapy" refers to a therapy targeting particular genes involved in tumor development. Possible gene therapy strategies include the restoration of defective cancer-inhibitory genes, cell transduction or transfection with antisense DNA corresponding to genes coding for growth factors and their receptors, or with the so-called 'suicide genes'.

Another aspect of the present invention includes a method for administering a compound of the present invention in combination with an immunotherapy. As used herein, "immunotherapy" refers to a therapy targeted to a particular protein involved in tumor development via antibodies specific to such protein. For example, monoclonal antibodies against vascular endothelial growth factor have been used in treating cancers.

Another aspect of the present invention includes a composition comprising a compound of Formula (I), or pharmaceutically acceptable salt thereof, in association with a pharmaceutically acceptable carrier. Compositions contemplated within this invention can be prepared according to conventional pharmaceutical techniques. A pharmaceutically acceptable carrier may also (but need not necessarily) be used in the composition of the invention.

The composition may take a wide variety of forms depending on the form of preparation desired for administration including, but not limited to, intravenous (both bolus and infusion), oral, nasal, transdermal, topical with or without occlusion, and injection intraperitoneally, subcutaneously, intramuscularly, intratumorally or parenterally, all using forms well known to those of ordinary skill in the pharmaceutical arts. The composition may comprise a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition may be presented in a form suitable for once-weekly or once-monthly administration; for example, an insoluble salt of the active compound, such as the decanoate salt, may be adapted to provide a depot preparation for intramuscular injection.

The phrase "pharmaceutically acceptable" refers to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use. In preparing the compositions in oral dosage form, one or more of the usual pharmaceutical carriers may be employed, including necessary and inert pharmaceutical excipients, such as water, glycols, oils, alcohols, flavoring agents, preservatives, coloring agents, syrup and the like; in the case of oral liquid preparations, carriers such as starches, sugars, diluents, granulating agents, lubricants, binders, disintegrating agents and the like may be employed.

The dosage unit (tablet, capsule, powder, injection, suppository, measured liquid dosage and the like) containing the pharmaceutical compositions herein will contain an amount of the active ingredient necessary to deliver a therapeutically effective amount as described above. The composition may contain from about 0.001 mg to about 5000 mg (preferably, from about 0.01 to about 500 mg) of the active compound or prodrug thereof and may be constituted into any form suitable for the mode of administration selected for a subject in need. A contemplated therapeutically effective amount may range from about 0.001 mg to 300 mg/kg of body weight per day. Preferably, the range is from about 0.03 to about 100 mg/kg of body weight per day. Most preferably, the range is from about 0.05 to about 15 mg/kg of body weight per day. The compounds may be administered according to a dosage regimen of from about 1 to about 5 times per day and still more preferably 1, 2 or 3 times a day.

For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages to be administered may be readily determined by those skilled in the art, and will vary depending on factors associated with the particular patient being treated (age, weight, diet and time of administration), the severity of the condition being treated, the compound being employed, the mode of administration and the strength of the preparation. The use of either daily administration or post-periodic dosing may be employed.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.001 to about 5000 mg of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

For oral administration in the form of a tablet or capsule, the active drug component can be optionally combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in which the compound of formula (I) may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations that generally contain suitable preservatives are employed when intravenous administration is desired.

As is also known in the art, the compounds may alternatively be administered parenterally via injection of a formulation consisting of the active ingredient dissolved in an inert liquid carrier. The injectable formulation can include the active ingredient mixed with an appropriate inert liquid carrier. Acceptable liquid carriers include vegetable oils such as peanut oil, cottonseed oil, sesame oil, and the like, as well as organic solvents such as solketal, glycerol, formal, and the like. As an alternative, aqueous parenteral formulations may also be used. For example, acceptable aqueous solvents include water, Ringer's solution and an isotonic aqueous saline solution. Further, a sterile non-volatile oil can usually be employed as a solvent or suspending agent in the aqueous formulation. The formulations are prepared by dissolving or suspending the active ingredient in the liquid carrier such that the final formulation contains from 0.005 to 10% by weight of the active ingredient. Other additives including a preservative, an isotonizer, a solubilizer, a stabilizer and a pain-soothing agent may adequately be employed.

Advantageously, compounds of Formula (I) may be administered in a single daily dose, or the total daily dosage may be administered in divided doses of two, three or four times daily. Furthermore, compounds of the present invention can be administered in intranasal form via topical use of suitable intranasal vehicles, or via transdermal routes, using those forms of transdermal skin patches or transdermal delivery vehicles well known to those of ordinary skill in that art. To be administered in the form of a transdermal delivery system, the dosage administration will, of course, be continuous rather than intermittent throughout the dosage regimen.

Because of their ease of administration, tablets and capsules represent an advantageous oral dosage unit form, wherein solid pharmaceutical carriers are employed. If desired, tablets may be sugarcoated or enteric-coated by standard techniques. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The compositions of the present invention also include a composition for slow release of the compound of the invention. The composition includes a slow release carrier (typically, a polymeric carrier) and a compound of the invention. In preparation for slow release, a slow release carrier, typically a polymeric carrier, and a compound of the invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the invention. Slow release biodegradable carriers are also well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50–200 nm in diameter, and most preferably about 100 nm in diameter).

The present invention also provides methods to prepare the pharmaceutical compositions of this invention. A compound of Formula (I) as the active ingredient is intimately admixed with a pharmaceutical carrier according to conventional pharmaceutical compounding techniques, which carrier may take a wide variety of forms depending on the form of preparation desired for administration. In preparing the compositions in oral dosage form, any of the usual pharmaceutical media may be employed. For solid oral dosage forms, suitable carriers and additives include starches, sugars, diluents, granulating agents, lubricants, binders, disintegrating agents and the like. For liquid oral preparations, suitable carriers and additives include water, glycols, oils, alcohols, flavoring agents, preservatives, coloring agents and the like. Additionally, liquid forms of the active drug component can be combined in suitably flavored suspending or dispersing agents such as the synthetic and natural gums, including for example, tragacanth, acacia, methyl-cellulose and the like. Other dispersing agents that may be employed include glycerin and the like.

Another aspect of the present invention includes a method for selectively treating or ameliorating a CDK related disorder, particularly a tumor, in a subject in need thereof comprising administering to the subject a therapeutically effective amount of a compound of Formula (I) or composition thereof conjugated to a targeting agent and delivered or "seeded" directly or indirectly into tissues with unregulated cyclin dependent kinase activity.

The term "delivered or "seeded" directly or indirectly into tissues" includes conjugating a compound of Formula (I) to a targeting agent which then directs the conjugate to its intended site of action (i.e., to vascular endothelial cells or to tumor cells). The term "targeting agent" includes the use of both antibody and non-antibody agents. Because of the specific interaction between the targeting agent and its corresponding binding partner, a compound of this invention can be administered with high local concentrations at or near a target site and thus treats the disorder at the target site more effectively.

An antibody targeting agent includes antibodies or antigen-binding fragments thereof, that bind to a targetable or accessible component of a tumor cell, tumor vasculature or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies or antigen-binding fragments thereof that bind to insoluble intracellular antigen(s) present in cells that may be induced to be permeable or in cell ghosts of substantially all tumor or normal cells, but are not present or accessible on the exterior of normal living cells of a mammal.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although a monoclonal antibody is preferred. There is a very broad array of antibodies known in the art that have immunological specificity for the cell surface of virtually any solid tumor type (see a Summary Table on monoclonal antibodies for solid tumors in U.S. Pat. No. 5,855,866, Thorpe, et al). Methods are known to those skilled in the art to produce and isolate antibodies to be used as targeting agents against tumors (U.S. Pat. No. 5,855,866, Thorpe); and, U.S. Pat. No. 6,342,219 (Thorpe)).

Non-antibody targeting agents include growth factors, such as PDGF, VEGF and FGF; peptides containing the tripeptide R-G-D, that bind specifically to the tumor vasculature and other targeting components such as annexins and related ligands. In addition, a variety of other organic molecules can also be used as targeting agents for tumors, examples are hyaluronan oligosaccharides which specifically recognize Hyaluronan-binding protein, a cell surface protein expressed during tumor cell and endothelial cell migration and during capillary-like tubule formation (U.S. Pat. No. 5,902,795 (Toole, et al.)) and polyanionic compounds, particularly polysulphated or polysulphonated compounds such as N- and O-sulfated polyanionic polysaccharides, polystyrene sulfonate and other polyanionic compounds (as described in U.S. Pat. No. 5,762,918 (Thorpe) which selectively bind to vascular endothelial cells.

Techniques for conjugating a therapeutic moiety to antibodies are well known (Amon, et al., Monoclonal Antibodies For Immunotargeting Of Drugs In Cancer Therapy, *Monoclonal Antibodies And Cancer Therapy,* Reisfeld, et al. (eds.), pp. 243–56 (Alan. R. Liss, Inc. 1985); Hellstrom, et al., Antibodies For Drug Delivery, *Controlled Drug Delivery* (2nd Ed.), Robinson, et al. (eds.), pp. 623–53 (Marcel Dekker, Inc. 1987); Thorpe, Antibody Carriers Of Cytotoxic Agents In Cancer Therapy: A Review, *Monoclonal Antibodies '84: Biological And Clinical Applications,* Pinchera, et al. (eds.), pp. 475–506 (1985)). Similar techniques can also be applied to attach compounds of the invention to non-antibody targeting agents. Those skilled in the art will know or be able to select methods in the art for forming conjugates with non-antibody targeting agents, such as oligopeptides, polysaccharides or other polyanionic compounds.

Although any linking moiety that is reasonably stable in blood can be used to link the compound of the invention to the targeting agent, those with biologically-releasable bonds and/or selectively cleavable spacers or linkers are preferred. "Biologically-releasable bonds" and "selectively cleavable spacers or linkers" refers to those linking moieties which have reasonable stability in the circulation and are releasable, cleavable or hydrolyzable only or preferentially under certain conditions, (i.e., within a certain environment or in contact with a particular agent). Such bonds include, for example, disulfide and trisulfide bonds and acid-labile bonds (as described in U.S. Pat. Nos. 5,474,765 and 5,762,918) and enzyme-sensitive bonds, including peptide bonds, esters, amides, phosphodiesters and glycosides (as described in U.S. Pat. Nos. 5,474,765 and 5,762,918). Such selective-release design features facilitate sustained release of the compounds from the conjugates at the intended target site.

The therapeutically effective amount of a compound of the invention conjugated to a targeting agent depends on the individual, the disease type, the disease state, the method of administration and other clinical variables. The effective amount is readily determinable using data from an animal model. Experimental animals bearing solid tumors are frequently used to optimize appropriate therapeutically effective amounts prior to translating to a clinical environment. Such models are known to be very reliable in predicting effective anti-cancer strategies. For example, mice bearing solid tumors are widely used in pre-clinical testing to determine working ranges of therapeutic agents that give beneficial anti-tumor effects with minimal toxicity.

The present invention further provides a composition that comprises an effective amount of the compound of the invention conjugated to a targeting agent and a pharmaceutically acceptable carrier. When proteins such as antibodies or growth factors, or polysaccharides are used as targeting agents, they are preferably administered in the form of injectable compositions. The injectable antibody solution will be administered into a vein, artery or into the spinal fluid over the course of from about 2 minutes to about 45 minutes, preferably from about 10 to about 20 minutes. In certain cases, intradermal and intracavitary administration are advantageous for tumors restricted to areas close to particular regions of the skin and/or to particular body cavities. In addition, intrathecal administrations may be used for tumors located in the brain.

Another aspect of the present invention includes a method for treating disorders related to unregulated CDK activity (in particular, restenosis, intimal hyperplasia or inflammation in vessel walls) in a subject in need thereof comprising administering to the subject by controlled delivery a therapeutically effective amount of a compound of Formula (I) or composition thereof coated onto an intraluminal medical device (in particular, a balloon-catheter or stent). Such devices are useful to prevent the occurrence of restenosis by inhibiting upregulated cyclin dependent kinase activity and thus preventing hyperproliferation of the endothelium.

The term "intraluminal medical device" refers to any delivery device, such as intravascular drug delivery catheters, wires, pharmacological stents and endoluminal paving. It is preferred that the delivery device comprises a stent that includes a coating or sheath which elutes or releases the compounds. The term "controlled delivery" refers to the release of active ingredient in a site-directed and time dependent manner. Alternatively, the delivery system for such a device may comprise a local infusion catheter that delivers the compound at a variably controlled rate.

The term "stent" refers to any device capable of being delivered by a catheter. A stent is routinely used to prevent vascular closure due to physical anomalies such as unwanted inward growth of vascular tissue due to surgical trauma. A stent often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent material may be a polymeric, metallic or a combination polymeric-metallic material and can be optionally biodegradable.

Commonly, a stent is inserted into the lumen in a non-expanded form and is then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in pending U.S. patent application 2002/0016625 A1 (Falotico, et al.) may also be utilized. The combination of a stent with drugs, agents or compounds which prevent inflammation and proliferation may provide the most efficacious treatment for post-angioplastry restenosis.

Compounds of the invention can be incorporated into or affixed to the stent in a number of ways and in utilizing any number of biocompatible materials. In one illustration, the compound is directly incorporated into a polymeric matrix, such as the polymer polypyrrole and subsequently coated onto the outer surface of the stent. Essentially, the compound elutes from the matrix by diffusion through the polymer molecules. Stents and methods for coating drugs on stents are discussed in detail in PCT application WO 96/32907. In another aspect, the stent is first coated with as a base layer comprising a solution of the compound, ethylene-co-vinylacetate and polybutylmethacrylate. The stent is then further coated with an outer layer comprising polybutylmethacrylate. The outlayer acts as a diffusion barrier to prevent the compound from eluting too quickly and entering the surrounding tissues. The thickness of the outer layer or topcoat determines the rate at which the compound elutes from the matrix. Stents and methods for coating are discussed in detail in pending U.S. patent application 2002/0016625 A1.

A solution of the compound of the invention and a biocompatible material or polymer may be incorporated into or onto a stent in a number of ways. For example, the solution may be sprayed onto the stent or the stent may be dipped into the solution and, in each case, allowed to then dry. Alternatively, the solution may be electrically charged to one polarity and the stent electrically changed to the opposite polarity. In this manner, the solution and stent will be attracted to one another. In using this type of spraying process, waste may be reduced and more control over the thickness of the coat may be achieved. The compound is usually only affixed to the outer surface of the stent (the surface which makes contact with the tissue), but for some compounds, the entire stent may be coated. The combination of the therapeutically effective amount of compound applied to the stent and the polymer coating controlling the release of the drug is important in the effectiveness of the drug. In one aspect, the compound remains on the stent for a period of about at least 6 months; in another aspect, for a period of about 3 days to about 6 months; and, in another aspect for a period of about 7 to about 30 days.

Any number of non-erodible biocompatible polymers may be utilized in conjunction with the compound of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium or shape-retentive polymeric materials that "remember" and return to their original shape upon activation at body temperature.

Methods for introducing a stent into a lumen of a body are well known. In an aspect of this invention, a compound-coated stent is introduced using a catheter. As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compounds for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells or by changes in the vascular resistance or lumen diameter. Optimum conditions can be determined based on data from animal model studies using routine computational methods.

The compounds of the present invention can also be administered in the form of liposome delivery systems, such as small unilamellar vesicles, large unilamellar vesicles and multilamellar vesicles. Liposomes containing delivery systems as well known in the art are formed from a variety of phospholipids, such as cholesterol, stearylamine or phosphatidylcholines.

Abbreviations

| | |
|---|---|
| "Boc₂O" | tert-butoxycarbonyl anhydride |
| "Cpd" | Compound |
| "CSCl₂" | thiophosgene |
| "DIC" | diisopropyl carbodiimide |
| "DMF" | N,N-dimethylformamide |
| "DPPA" | diphenylphosphorylazide |
| "EDCI" | ethyl dimethylaminopropyl carbodiimide |
| "HOBT" | hydroxybenzyl triazole |
| "NH₂NH₂" | hydrazine |
| "Pd" | palladium (II) |
| "Ph" | phenyl |
| "rt" | room temperature |
| "TBAF" | tetrabutylammonium fluoride |
| "t-BuOH" | tert-butanol |
| "TFA" | trifluoroacetic acid |
| "THF" | tetrahydrofuran |

Nomenclature

Compounds can be named according to nomenclature well known in the art or names can be generated using commercial chemical naming software such as ACD/Index Name (Advanced Chemistry Development, Inc., Toronto, Ontario).

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

In Scheme A, a Compound A1, (optionally substituted with 1 to 4 substituents selected from $R_2$; wherein the $R_2$ group includes a halogen atom (such as Cl, Br or I) or a dioxo alkyl chain (such as —OCH$_2$CH$_2$O—; wherein the ends of the chain occupy 2 carbon positions on the ring); and, wherein the aniline nitrogen atom was protected with a suitable protecting group) was coupled with a di-halo (preferably chlorine) substituted Compound A2 (optionally substituted with an additional substituent selected from $R_1$) using NaH to give Compound A3.

A carboxyl substituted Compound A4 (wherein Q is selected from a halogen such as Cl, Br or I; wherein X, Y and Z are dependently selected from at least one carbon atom and at least one nitrogen atom; and, wherein a nitrogen atom may simultaneously occupy only the X and Z positions) was aminated by Curtius rearrangement using t-BuOH and DPPA to produce a protected amine Compound A5. Compound A5 was alkylated with a suitably protected bromine substituted $C_{2-5}$alkyl chain (such as, in this case, by using a tert-butyldimethylsilane protecting group) to produce Compound A6. The heteroaryl ring Compound A6 was then reacted with the triazine ring Compound A3 using a palladium-metal catalyzed cross-coupling reaction (wherein Q is converted to a SnMe$_3$ substituent from Cl, Br or I). The target Compound A7 was then deprotected using TFA.

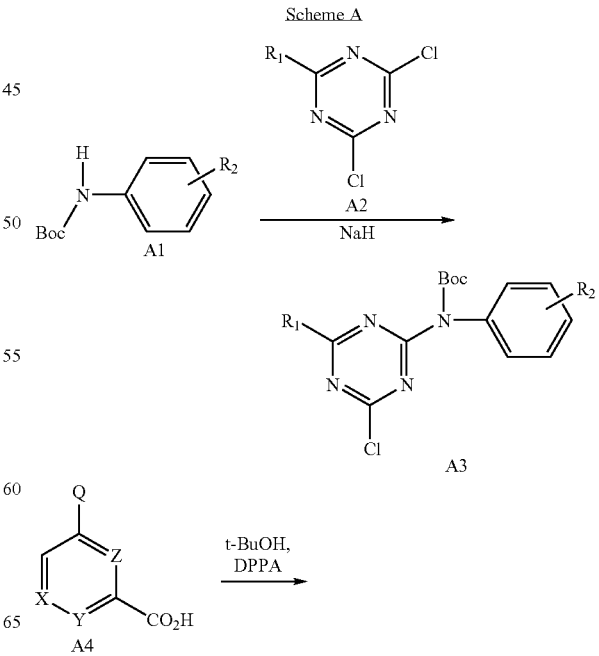

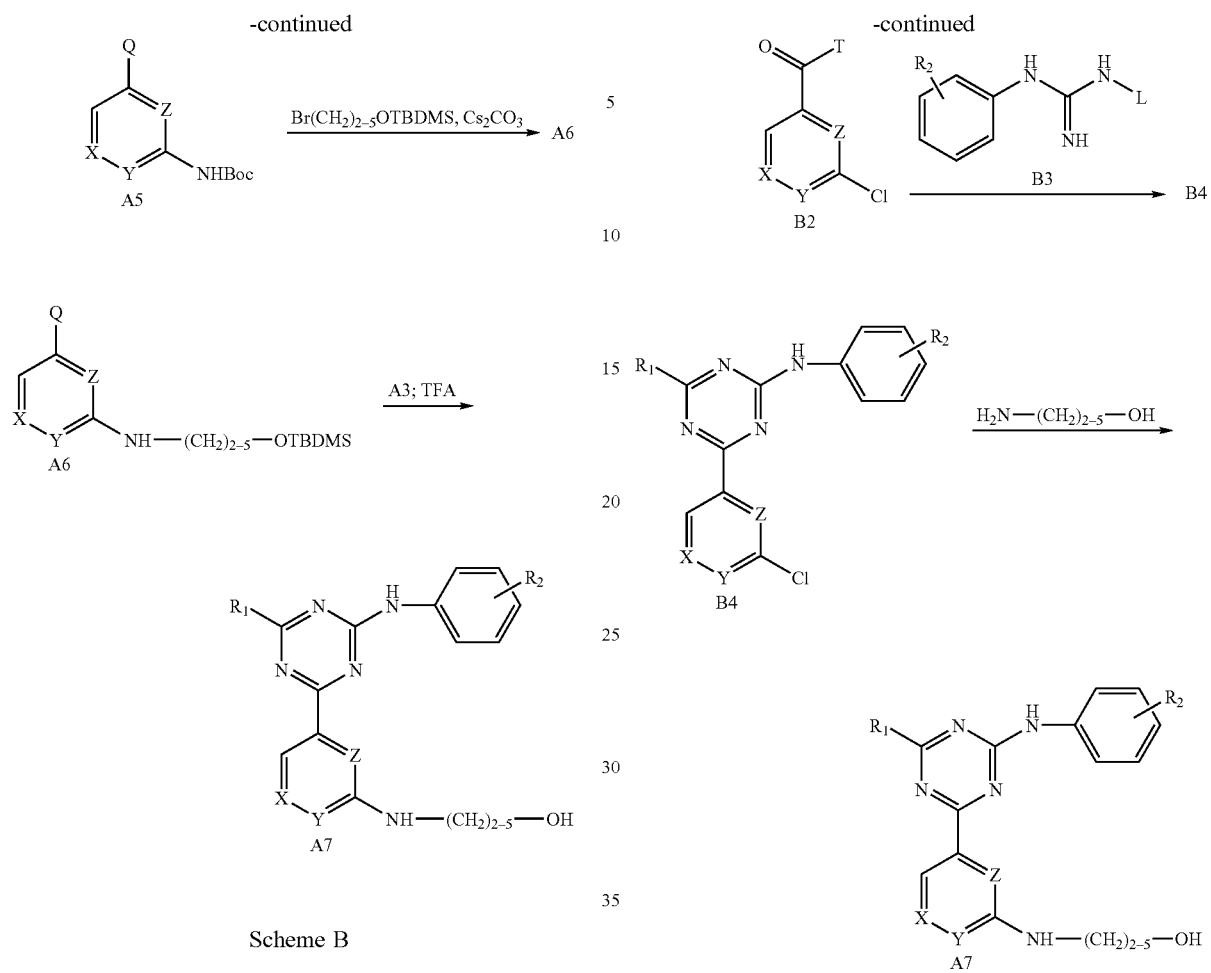

Scheme B

In Scheme B, a Compound B1 (substituted with S; wherein S is selected from NH$_2$ or OH) was halogenated with SOCl$_2$ in the presence of a suitable solvent (when S is selected from OH) or further aminated using N,N-dimethylformamide dimethyl acetal (when S is selected from NH$_2$) to produce Compound B2 (substituted with T; wherein T is selected from Cl after halogenation or as a mixture of stereoisomers of N=CH—N(Me)$_2$ after amination), which may be isolated or used directly to prepare Compound B4.

The triazine ring is formed on Compound B2 by condensation using Compound B3 (substituted with L as the terminal group on the nitrogen atom; wherein L is selected from hydrogen or —C(=NH)(R$_1$) and optionally substituted with an additional R$_2$ substituent on the phenyl ring) in the presence of an alkylamine or KtBuOH to produce a substituted triazine Compound B4. Amination with an aminoalkanol gave the target Compound A7.

Scheme B

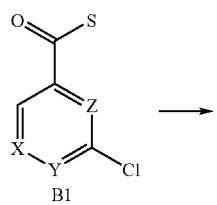

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

$^1$H and $^{13}$C NMR spectra were measured on a Bruker AC-300 (300 MHz) spectrometer using tetramethylsilane and DMSO respectively as internal standards. Elemental analyses were obtained by Quantitative Technologies Inc. (Whitehouse, N.J.), and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ES) were recorded on a Hewlett Packard 59987A spectrometer.

Example 1

3-((5-(4-((3-chlorophenyl)amino)-1,3,5-triazin-2-yl)-3-pyridinyl)amino)-1-propanol (Compound 1)

3-Chloroaniline (29.4 g, 229 mmol) was dissolved in THF (250 mL) at 20° C. A THF solution (80 mL) of Boc$_2$O (50 g, 229 mmol) was added slowly to the mixture of 3-chloroaniline and THF. The resulting mixture was stirred for 3 days and then concentrated. The crude product was purified by recrystallization from EtOAc/Hexane three times to give Compound 1A (40.4 g, 78%) as a white solid. $^1$H NMR (300 MHz, CDCl$_3$) δ 7.52 (s, 1H), 7.17 (m, 2H), 7.00 (dt, J=7.4, 1.8 Hz, 1H), 6.49 (s, 1H), 1.52(s, 9H); MS (ES) m/z: 250 (M+Na). Anal. Calcd. For C$_{11}$H$_{14}$NO$_2$Cl: C, 58.03; H, 6.20; N, 6.15. Found: C, 58.14; H, 6.22; N, 6.10. THF (150 mL) was added to a mixture of Compound 1A (5.5 g, 24.2 mmol) and NaH (60% in mineral oil, 2.4 g, 60.6 mmol) at 0° C. under N$_2$. The mixture was stirred at 20° C. for 1 h and then cooled to 0° C. and Compound 1B (6.2 g, 41.2 mmol; prepared as described in Harris, R. L. N. *Synthesis* 1981, 907) was added. After the mixture was stirred at 20° C. overnight, the solvent was evaporated and the residue was purified by flash chromatography (10% EtOAc in hexanes) to give Compound 1C (4.3 g, 52%) as a white solid. $^1$H NMR (300 MHz, CDCl$_3$) δ 8.72 (s, 1H), 7.40 (m, 2H), 7.22 (brs, 1H), 7.11 (m, 1H), 1.48 (s, 9H); MS (ES) m/z: 363 (M+Na). Anal. Calcd. For C$_{14}$H$_{14}$N$_4$O$_2$Cl$_2$: C, 49.28; H, 4.14; N, 16.42. Found: C, 49.52; H, 4.13; N, 16.41.

A mixture of 5-bromonicotinic acid Compound 1D (10 g, 49.5 mmol), t-BuOH (100 mL), triethylamine (15.2 g, 150 mmol) and DPPA (20.4 g, 74 mmol) in toluene (100 mL) was stirred at 65° C. for 40 min and then warmed to 100° C. for 22 h under nitrogen. The mixture was cooled and concentrated under vacuum. The crude product was purified by column chromatography on SiO$_2$ eluting with ethyl acetate/hexane to give Compound 1E (10.52 g, 78%) as a white solid. $^1$H NMR (300 MHz, CDCl$_3$) δ 8.32 (m, 3H), 6.97 (brs, 1H), 1.53 (s, 9H); MS (ES) m/z: 273, 275 (M+H$^+$). Anal. Calcd. For C$_{10}$H$_{13}$N$_2$O$_2$Br: C, 43.98; H, 4.80; N, 10.26. Found: C, 43.88; H, 4.52; N, 10.20. A mixture of Compound 1E (2.85 g, 10.44 mmol), (3-bromopropoxy)-t-butyldimethylsilane (3.96 g, 15.66 mmol) and Cs$_2$CO$_3$ (10.21 g, 31.3 mmol) in anhydrous DMF (55 mL) was stirred at 70° C. for 23 h under nitrogen. The mixture was cooled, diluted with water and extracted with ether (3×). The organic phase was dried (Na$_2$SO$_4$) and concentrated. The product was purified by column chromatography (eluting with EtOAc/hexane) to give Compound 1F (4.2 g, 90%) as a yellow oil. $^1$H NMR (300 MHz, CDCl$_3$) δ 8.45 (brs, 2H), 7.77 (brs, 1H), 3.73 (brt, J=7.3 Hz, 2H), 3.62 (t, J=5.9 Hz, 2H), 1.81 (m, 2H), 1.45 (s, 9H), 0.84 (s, 9H), 0.00 (s, 6H); MS (ES) m/z: 445, 447 (M+H$^+$). Anal. Calcd. For C$_{19}$H$_{33}$N$_2$O$_3$BrSi: C, 51.23; H, 7.47; N, 6.29. Found: C, 51.45; H, 7.47; N, 6.53.

n-BuLi (2.3 mL, 2.5 M, 5.65 mmol) was added dropwise to a solution of Compound 1F (1.26 g, 2.82 mmol) in anhydrous THF (10 mL) at −78° C. and the mixture was stirred for 20 min. Anhydrous zinc chloride (8.47 mL, 1 M in ether, 8.47 mmol) was added dropwise to the THF solution containing Compound 1F at −78° C. and stirred for 10 min before it was warmed to 20° C. by removing the dry-ice bath. A mixture of Compound 1C (640 mg, 1.88 mmol) and Pd(PPh$_3$)$_4$ (109 mg, 0.094 mmol) in dry THF (8 mL) was added. The resulting mixture was stirred at 20° C. for 10 min, then at 70° C. for 22 h and the solvent was removed under vacuum. The residue was partitioned between water and ether and then separated. The aqueous layer was extracted with ether (3×). The combined organic layers were dried (Na$_2$SO$_4$) and concentrated. The product (a mixture of bis-Boc- and mono-Boc-protected coupling products) was purified by column chromatography to give 458 mg of yellow foam. The yellow foam was mixed with TFA (5 mL) and the mixture was stirred at 20° C. for 2 h and then concentrated. NH$_4$OH was added, followed by water addition until the pH of the aqueous layer reached about 10–11. A yellow solid was formed, collected through filtration and then dried under vacuum. The product was purified by column chromatography to give Compound 1 (208 mg, 73%) as a yellow solid. $^1$H NMR (300 MHz, DMSO-d$_6$) δ 10.55 (s, 1H), 8.89 (s, 1H), 8.18 (brs, 1H), 8.06 (s, 1H), 7.76 (s, 1H), 7.71 (d, J=8.0 Hz, 1H), 7.41 (t, J=8.0 Hz, 1H), 7.15 (d, J=7.9 Hz, 1H), 6.19 (brs, 1H), 4.54 (t, J=5.0 Hz, 1H), 3.55 (m, 2H), 3.18 (m, 2H), 1.80 (m, 2H); MS (ES) m/z: 357 (M+H$^+$). Anal. Calcd. For C$_{17}$H$_{17}$N$_6$OCl.0.35H$_2$O: C, 56.23; H, 4.91; N, 23.14. Found: C, 56.63; H, 4.78; N, 22.76.

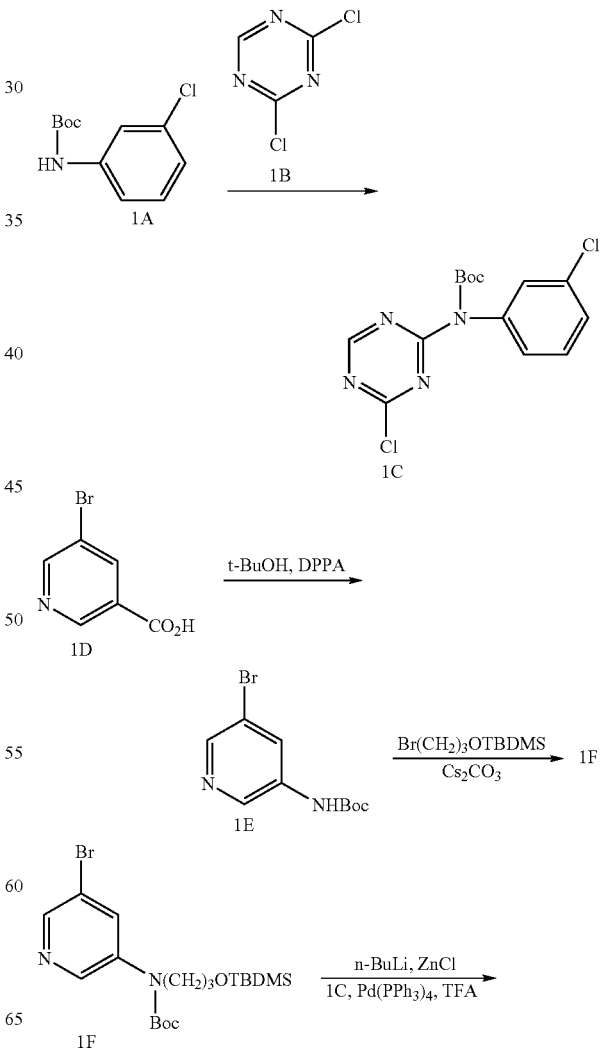

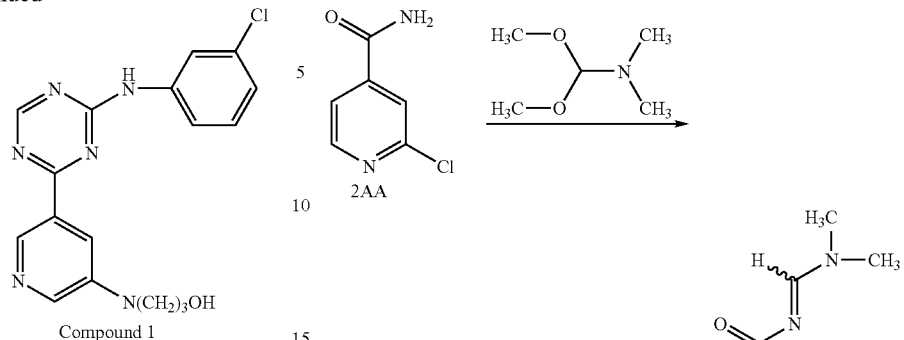

Compound 1

Example 2

3-((4-(4-((3-chlorophenyl)amino)-1,3,5-triazin-2-yl)-2-pyridinyl)amino)-1-propanol (Compound 2)

Compound 2 may be prepared using a variety of methods as herein described.

Method 2A:

A mixture of 2-chloroisonicotinamide 2AA (4.0 g, 25.6 mmol) and N, N-dimethylformamide dimethyl acetal (3.66 g, 30.7 mmol) was heated at 100° C. for 1 h under nitrogen and then concentrated under vacuum. The residue was purified by column chromatography (EtOAc/hexane) to give Compound 2AB (a mixture of the E and Z isomers) (3.3 g, 61%) as a white solid. $^1$H NMR (300 MHz, DMSO-d$_6$) δ 8.69 (s, 1H), 8.55 (d, J=5.0 Hz, 1H), 8.52 (d, J=5.0 Hz, 0.25H), 7.98–7.87 (m, 2H), 7.56 (s, 0.25H), 7.43 (dd, J=5.0, 1.2 Hz, 0.25H), 3.25 (s, 3H), 3.18 (s, 3H), 2.99 (s, 0.9H), 2.86 (s, 0.9H); Anal. Calcd. For C$_9$H$_{10}$ClN$_3$O.0.1H$_2$O: C, 50.64; H, 4.82; N, 19.69. Found: C, 50.79; H, 4.69; N, 19.73. A mixture of (3-chloro-phenyl)-guanidine nitrate Compound 2AC (prepared as described in J. Med. Chem., 18, 1975, 1077–1088) (198 mg, 0.85 mmol), potassium t-butoxide and THF (3 mL) was stirred at 20° C. for 15 min. Compound 2AB (72 mg, 0.34 mmol) was added in one portion and the mixture was stirred at 20° C. for 15 min and then at 70° C. for 15 min. The mixture was concentrated under vacuum. The product was purified by column chromatography (EtOAc/hexane) to give Compound 2AD (26 mg, 24%) as a solid. $^1$H NMR (300 MHz, DMSO-d$_6$) δ 10.73 (s, 1H), 8.99 (s, 1H), 8.67 (d, J=5.1 Hz, 1H), 8.20 (d, J=5.1 Hz, 1H), 7.98 (t, J=2.0 Hz, 1H), 7.69 (d, J=8.3 Hz, 1H), 7.42 (t, J=8.1 Hz, 1H), 7.18 (d, J=7.8 Hz, 1H); Anal. Calcd. For C$_{14}$H$_9$Cl$_2$N$_5$.0.1H$_2$O: C, 52.55; H, 2.91; N, 21.89. Found: C, 52.61; H, 2.77; N, 21.66. A mixture of Compound 2AD (124 mg, 0.39 mmol) and 3-amino-1-propanol (3.5 mL) was heated at 85° C. for 18 h. After water (60 mL) was added to the mixture, it was extracted with EtOAc. The organic extract was concentrated under vacuum. The residue was purified by column chromatography to give Compound 2 (14 mg, 10%) as a yellow solid. $^1$H NMR (300 MHz, DMSO-d$_6$) δ 10.58 (s, 1H), 8.93 (s, 1H), 8.16 (d, J=5.3 Hz, 1H), 7.98 (s, 1H), 7.76 (brs, 1H), 7.42 (m, 2H), 7.29 (dd, J=5.3, 1.2 Hz, 1H), 7.16 (dd, J=8.0, 1.3 Hz, 1H), 6.85 (t, J=5.5 Hz, 1H), 4.50 (t, J=5.2 Hz, 1H), 3.50 (q, J=6.2 Hz, 2H), 3.34 (m, 2H), 1.72 (m, 2H); Anal. Calcd. For C$_{17}$H$_{17}$ClN$_6$O.1.2H$_2$O: C, 53.93; H, 5.17; N, 22.21. Found: C, 54.03; H, 4.97; N, 21.95

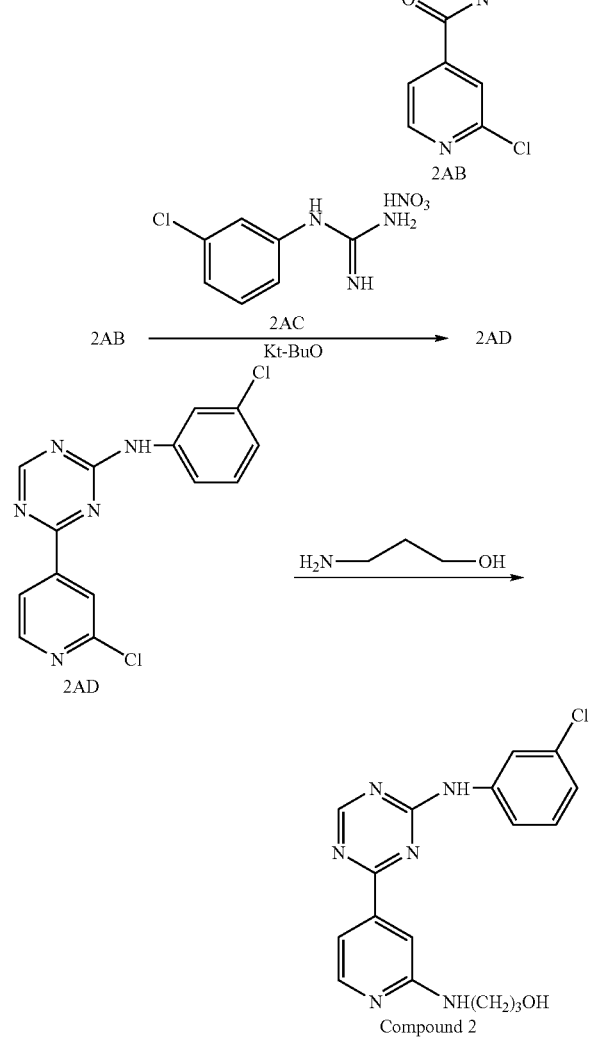

Compound 2

Alternatively, the intermediate 2AB need not be isolated, allowing the triazine ring (Compound 2AD) to form in one step. A mixture of Compound 2AA (22.5 g, 0.144 mol) and N, N-dimethylformamide dimethyl acetal (20.6 g, 0.173 mol) was heated at 100° C. for 70 min under nitrogen and then concentrated under high vacuum. The mixture was kept under vacuum until it solidified to give the crude Compound 2AB. After (3-chloro-phenyl)-guanidine nitrate Compound 2AC (33.5 g, 0.144 mol) and potassium t-butoxide (16.18 g, 0.144 mol) were added to the crude Compound 2AB, THF (750 mL) was added and the mixture was stirred at 20° C. for 2 h. EtOAc (500 mL) and water (2 L) were added to the mixture. The layers were separated and the organic layer was washed with water (2×200 mL) and then dried over $Na_2SO_4$. After the drying agent was filtered off, silica gel was added to the filtrate (540 mL). The mixture of filtrate and silica gel was concentrated under vacuum and then dry-loaded onto a flash chromatography column. The column was eluted with Hexane/EtOAc (2:1) and 6.0 g of partially purified Compound 2AD was isolated. 3-Amino-1-propanol (150 mL) was added to the impure Compound 2AD and the mixture was heated at 90° C. for 16 h and then poured into water (1L). The solids that precipitated were filtered and washed with water (2×). Compound 2 (906 mg, 2%) was recrystallized from EtOAc (2×) as a yellow solid.

Method 2B:

A mixture of Compound 2BA (1.00 g, 3.30 mmol; prepared as described in Lohse, O. *Synth. Commun.* 1996, 26, 2017), DPPA (1.36 g, 4.95 mmol) and triethylamine (1.4 mL, 10 mmol) in t-BuOH (5.5 mL) and toluene (5 mL) was heated at 65° C. for 1.5 h, then warmed to 100° C. for 4 h. After concentration, the mixture was purified by flash chromatography (EtOAc/hexane) to give Compound 2BB (515 mg, 50%) as a white solid. $^1H$ NMR (300 MHz, $CDCl_3$) δ 9.17 (brs, 1H), 8.48 (s, 1H), 7.98 (dd, J=5.2, 1.5 Hz, 1H), 7.34 (dd, J=5.2, 1.3 Hz, 1H), 1.56 (s, 9H); MS (ES) m/z: 343 (M+Na). A mixture of Compound 2BB (330 mg, 1.03 mmol), (3-bromopropoxy)-tert-butyldimethylsilane (340 mg, 1.34 mmol) and $Cs_2CO_3$ (504 mg, 1.55 mmol) in dry DMF (4 mL) was stirred at 70° C. for 3 h. After the solvent was evaporated under reduced pressure, the residue was purified by column chromatography (EtOAc/hexane) to provide Compound 2BC (450 mg, 89%) as clear oil. $^1H$ NMR (400 MHz, $CDCl_3$) δ 8.11 (s, 1H), 8.00 (d, J=5.2 Hz, 1H), 7.33 (dd, J=5.2, 1.3 Hz, 1H), 3.99 (t, J=7.3 Hz, 2H), 3.65 (t, J=6.3 Hz, 2H), 1.84 (m, 2H), 1.52 (s, 9H), 0.87 (s, 9H), 0.02 (s, 6H); MS (ES) m/z: 515 (M+Na).

A mixture of Compound 2BC (650 mg, 1.32 mmol), bis(trimethyltin) (870 mg, 2.66 mmol), tetrakis(triphenylphosphine)palladium (150 mg, 0.130 mmol), LiCl (170 mg, 4.00 mmol) and 2,6-di-tert-butyl-4-methylphenol (12 mg, 0.054 mmol) in anhydrous 1,4-dioxane (12 mL) was heated at 90° C. for 1.5 h under nitrogen. The solvent was removed under reduced pressure and the residue was purified by column chromatography on silica gel (EtOAc/hexane) to give Compound 2BD (590 mg, 84%) as clear oil. $^1H$ NMR (300 MHz, $CDCl_3$) δ 8.09 (d, J=4.7 Hz, 1H), 7.56 (s, 1H), 7.10 (d, J=4.7 Hz, 1H), 3.97 (t, J=7.2 Hz, 2H), 3.64 (t, J=6.5 Hz, 2H), 1.85 (m, 2H), 149 (s, 9H), 0.86 (s, 9H), 0.33 (s, 9H), 0.00 (s, 6H); MS (ES) m/z: 527 (M−H$^+$). Anal. Calcd. For $C_{22}H_{42}N_2O_3SiSn$: C, 49.92; H, 8.00; N, 5.29. Found: C, 50.32; H, 7.88; N, 5.20. A mixture of Compound 1C (590 mg, 1.73 mmol), $Pd_2(dba)_3$ (160 mg, 0.175 mmol), $AsPh_3$ (424 mg, 1.39 mmol) and 2,6-di-tert-butyl-4-methylphenol (24 mg, 0.11 mmol) was degassed under high vacuum and then filled with $N_2$. This process was repeated three times. Toluene (20 mL) was added and the mixture was stirred at 20° C. for about 30 min. A solution of Compound 2BD (915 mg, 1.73 mmol) in toluene (20 mL) was added and the mixture was heated at 100° C. for 3.5 h. After removal of solvent, the residue was purified by flash chromatography (EtOAc/hexane) to give Compound 2BE (895 mg, 77%) as clear oil. $^1H$ NMR (300 MHz, $CDCl_3$) δ 9.05 (s, 1H), 8.51 (s, 1H), 8.48 (d, J=5.1 Hz, 1H), 7.80 (dd, J=5.2, 1.4 Hz, 1H), 7.41–7.39 (m, 2H), 7.28–7.27 (m, 1H), 7.16 (m, 1H), 4.05 (t, J=7.3 Hz, 2H), 3.66 (t, J=6.3 Hz, 2H), 1.87 (m, 2H), 1.51 (s, 9H), 1.50 (s, 9H), 0.86 (s, 9H), 0.01 (s, 6H); MS (ES) m/z: 670 (M+H$^+$).

$CF_3COOH$ (10 mL) was added to a solution of Compound 2BE (1.74 g, 2.59 mmol) in $CH_2Cl_2$ (10 mL). After the mixture was stirred at 20° C. for 2 h, it was concentrated. Saturated ammonium hydroxide was added to the residue until the pH of the mixture was greater than 7. The precipitated solid was collected through filtration and washed with ice water. The crude product was purified by recrystallization from EtOAc to give Compound 2 (750 mg, 81%) as a yellow solid. $^1H$ NMR (300 MHz, DMSO-$d_6$) δ 10.59 (s, 1H), 8.92 (s, 1H), 8.15 (d, J=6.5 Hz, 1H), 7.97 (s, 1H), 7.75 (brs, 1H), 7.43 (m, 2H), 7.30 (d, J=6.5 Hz, 1H), 7.16 (d, J=6.5 Hz, 1H), 6.96 (brs, 1H), 4.52 (brs, 1H), 3.50 (t, J=6.3 Hz, 2H), 3.30 (m, 2H), 1.74 (m, 2H); MS (ES) m/z: 357 (M+H$^+$).

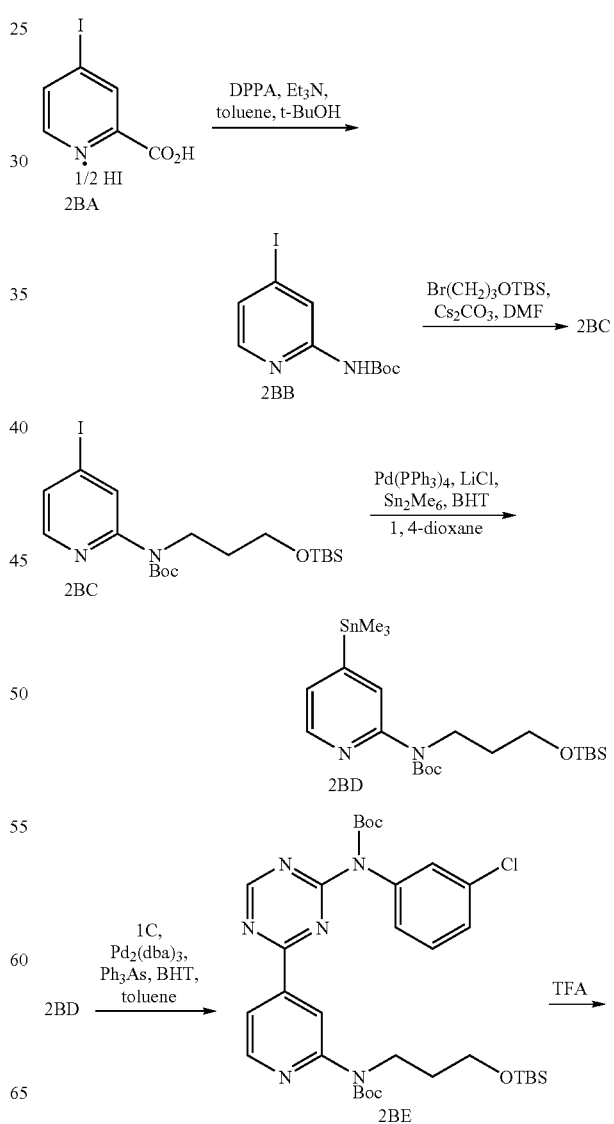

-continued

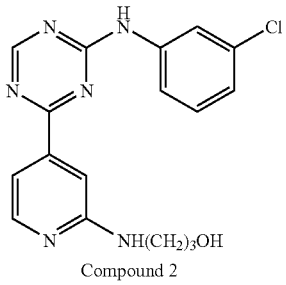

Compound 2

Example 3

3-((6-(4-((3-chlorophenyl)amino)-1,3,5-triazin-2-yl)pyrazin-2-yl)amino)-1-propanol (Compound 3)

A mixture of Compound 3A (220 mg, 1.39 mmol; prepared as described in Sato, N. *J. Heterocyc. Chem.* 1994, 31, 1177), DPPA (575 mg, 2.09 mmol) and triethylamine (0.39 mL, 2.80 mmol) in t-BuOH (3 mL) and toluene (2 mL) was heated at 65° C. for 1.5 h, then at 85° C. for 2 h. After concentration, the mixture was purified by flash chromatography (EtOAc/hexane) to give Compound 3B (180 mg, 57%) as a white solid. $^1$H NMR (300 MHz, CDCl$_3$) δ 9.19 (s, 1H), 8.26 (s, 1H), 7.17 (brs, 1H), 1.54 (s, 9H). A mixture of Compound 3B (160 mg, 0.697 mmol), (3-bromopropoxy)-tert-butyldimethylsilane (220 mg, 0.870 mmol) and Cs$_2$CO$_3$ (340 mg, 1.04 mmol) in dry DMF (2 mL) was stirred at 60° C. for 2.5 h. The solvent was evaporated under reduced pressure and the residue was purified by column chromatography (EtOAc/hexane) to provide Compound 3C (262 mg, 94%) as clear oil. $^1$H NMR (300 MHz, CDCl$_3$) δ 9.01 (s, 1H), 8.20 (s, 1H), 4.00 (t, J=7.4 Hz, 2H), 3.68 (t, J=6.2 Hz, 2H), 1.87 (m, 2H), 1.54 (s, 9H), 0.87 (s, 9H), 0.03 (s, 6H).

A mixture of Compound 3C (123 mg, 0.306 mmol), bis(trimethyltin) (200 mg, 0.611 mmol), tetrakis(triphenylphosphine)palladium (35 mg, 0.030 mmol), LiCl (40 mg, 0.94 mmol) and 2,6-di-tert-butyl-4-methylphenol (3 mg, 0.014 mmol) in anhydrous 1,4-dioxane (2 mL) was refluxed for 4 h under nitrogen. The solvent was removed under reduced pressure and the residue was purified by chromatography on silica gel (EtOAc/hexane) to give Compound 3D (154 mg, 95%) as clear oil. $^1$H NMR (300 MHz, CDCl$_3$) δ 8.79 (s, 1H), 8.21 (s, 1H), 4.01 (t, J=7.2 Hz, 2H), 3.67 (t, J=6.0 Hz, 6.0 Hz, 2H), 1.90 (m, 2H), 1.53 (s, 9H), 0.87 (s, 9H), 0.36 (s, 9H), 0.02 (s, 6H); MS (ES) m/z: 531 (M+H$^+$). A mixture of Compound 3D (73 mg, 0.14 mmol), Compound 1C (52 mg, 0.15 mmol), dichlorobis(triphenylphosphine)palladium (15 mg, 0.021 mmol) and LiCl (18 mg, 0.42 mmol) in anhydrous toluene (3 mL) was stirred at 100° C. overnight under nitrogen. The mixture was cooled, concentrated under vacuum and purified by flash chromatography (EtOAc/hexane) to give the coupled product as yellow oil. TFA (1 mL) was added and the mixture was stirred at 20° C. for 4 h. After it was concentrated, saturated NH$_4$OH solution and water were added until the mixture turned basic. After the precipitated solid was collected through filtration, it was washed with water and Et$_2$O and dried under vacuum to provide Compound 3 (1.5 mg, 47%) as a yellow solid. $^1$H NMR (300 MHz, DMSO-d$_6$) δ 10.59 (s, 1H), 8.91 (s, 1H), 8.63 (s, 1H), 8.20 (brs, 1H), 8.12 (s, 1H), 7.80 (brs, 1H), 7.39 (t, J=8.2 Hz, 1H), 7.34 (brs, 1H), 7.13 (d, J=7.8 Hz, 1H), 4.60 (m, 1H), 3.50 (m, 2H), 3.32 (m, 2H), 1.76 (t, J=6.4 Hz, 2H); MS (ES) m/z: 358 (M+H$^+$).

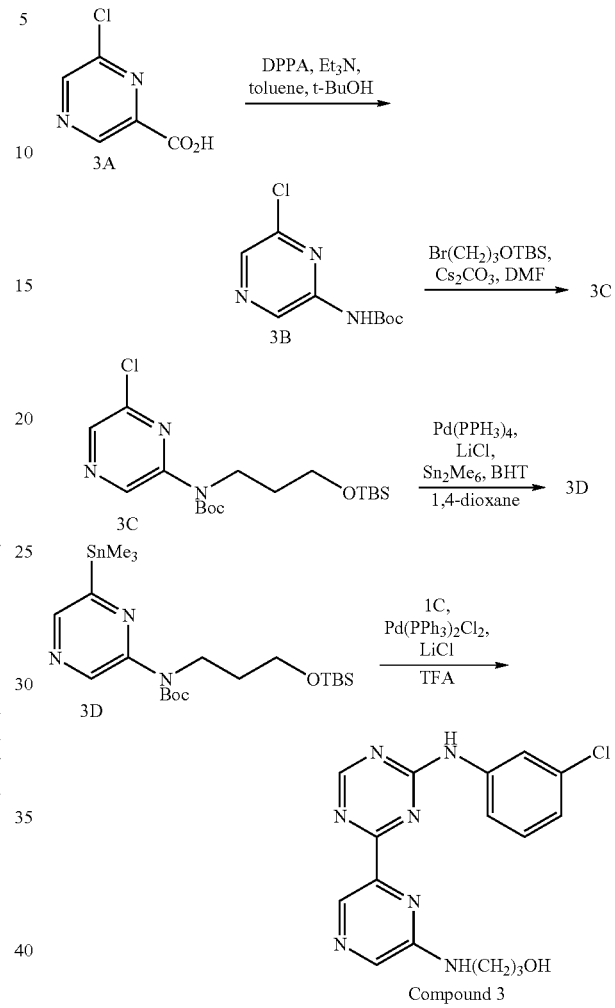

Compound 3

Example 4

3-((4-(4-amino-6-((3-chlorophenyl)amino)-1,3,5-triazin-2-yl)-2-pyridinyl)amino)-1-propanol (Compound 4)

2-Chloroisonicotinic acid Compound 4A (1.49 g, 9.45 mmol) was added to a solution of thionyl chloride (1.33 mL) in toluene (4.3 mL). DMF (one drop) was added and the mixture was refluxed for 18 h. The excess thionyl chloride was removed by distillation to give Compound 4B. THF (4 mL) was added to Compound 4B and the mixture was cooled in an ice bath. (3-chlorophenyl)biguanide HCl Compound 4C (prepared as described in *Arch. Ital. Patol. Clin. Tumori*, 1967, 10(3–4), 211–22) (2.69 g, 9.45 mmol) was added in one portion. Et$_3$N (4.3 mL, 31.0 mmol) was added dropwise and the mixture was stirred at 20° C. for 18 h. Water (10 mL) was added and the mixture was stirred at 20° C. for 3 h, then poured into a mixture of water (50 mL) and dichloromethane (50 mL). After the solid was filtered, the dichloromethane layer was concentrated under vacuum. The resulting residue was combined with the solids and chromatographed on silica gel (CH$_2$Cl$_2$/MeOH). Compound 4D and an unknown compound (100 mg) with the same $R_f$ (~0.5, CH$_2$Cl$_2$/MeOH=9/1) were isolated. MS (ES) m/z: 334 (M+H$^+$). The yellow compounds were heated with 3-amino-1-propanol (1.6 mL) at 100° C. for 4 days. NaHCO$_3$ (25 mg) was added and the excess 3-amino-1-propanol was removed by distillation under reduced pressure. The residue was purified by flash chromatography (CH$_2$Cl$_2$/MeOH) to give Compound 4 (30 mg, 0.06%) as a yellow solid. $^1$H NMR (300 MHz, CD$_3$OD) δ 8.02 (d, J=5.5 Hz, 1H), 7.96 (t, J=2.0 Hz, 1H), 7.63 (d, J=8.2 Hz, 1H), 7.43 (s, 1H), 7.39 (d, J=6.1 Hz, 1H), 7.28 (t, J=8.1 Hz, 1H), 7.02 (d, J=9.1 Hz, 1H), 3.68 (t, J=6.1 Hz, 2H), 3.43 (t, J=6.8 Hz, 2H), 1.85 (m, 2H); MS (ES) m/z: 372 (M+H$^+$).

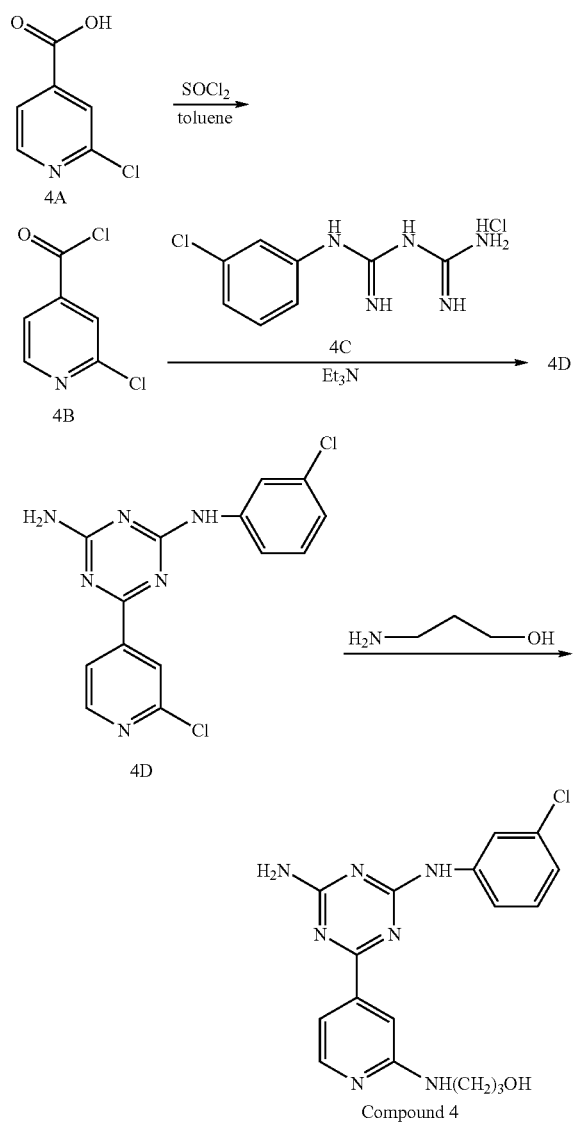

Example 5

3-((5-(4-((2,3-dihydro-1,4-benzodioxin-6-yl)amino)-1,3,5-triazin-2-yl)-3-pyridinyl)amino)-1-propanol (Compound 5)

1,4-Benzodioxan-6-amine (4.23 g, 28.0 mmol) was dissolved in THF (50 mL) at 20° C. A THF solution (10 mL) of Boc$_2$O (6.1 g, 28.0 mmol) was added slowly to the mixture of 1,4-benzodioxan-6-amine and THF and the resulting mixture was stirred for 18 h. After the solvent was removed by concentration, the crude product was purified by recrystallization from EtOAc/hexane to give Compound 5A (4.97 g, 71%) as a white solid. $^1$H NMR (300 MHz, CDCl$_3$) δ 6.95 (s, 1H), 6.77 (s, 2H), 6.29 (brs, 1H), 4.22 (s, 4H), 1.50 (s, 9H); MS (ES) m/z: 274 (M+Na). Anal. Calcd. For C$_{13}$H$_{17}$NO$_4$: C, 62.14; H, 6.82; N, 5.57. Found: C, 62.03; H, 6.69; N, 5.48. THF (3.2 mL) was added to a mixture of Compound 5A (90 mg, 0.360 mmol) and NaH (36 mg, 60%, 0.90 mmol) at 0° C. under nitrogen. After the mixture was stirred at 0° C. for 5 min, it was warmed to 20° C. for 1 h, then cooled back to 0° C. Compound 1B (59.4 mg, 0.40 mmol) was added and the mixture was stirred at 20° C. for 20 h. NH$_4$Cl was added and the mixture was concentrated. The residue was extracted with EtOAc (3×). The organic extracts were combined, dried (Na$_2$SO$_4$) and concentrated. The product was purified by column chromatography (EtOAc/hexane) to give Compound 5B (80 mg, 57%) as a solid. $^1$H NMR (300 MHz, CDCl$_3$) δ 8.69 (s, 1H), 6.91 (d, J=8.5 Hz, 1H), 6.73–6.66 (m, 2H), 4.29 (s, 4H), 1.49 (s, 9H); MS (ES) m/z: 387 (M+Na). Anal. Calcd. For C$_{16}$H$_{17}$N$_4$O$_4$Cl: C, 52.68; H, 4.70; N, 15.36. Found: C, 52.72; H, 4.67; N, 15.17.

n-BuLi (3.03 mL, 2.5 M, 7.6 mmol) was added dropwise to Compound 1F (1.71 g, 3.79 mmol) in anhydrous THF (12.6 mL) at −78° C. and stirred for 20 min. Anhydrous zinc chloride (11.4 mL, 1 M in ether, 11.4 mmol) was added dropwise to the THF solution containing Compound 1F at −78° C., then stirred for 10 min before the mixture was warmed to 20° C. by removing the dry-ice bath. A mixture of Compound 5B (691 mg, 1.90 mmol) and Pd(PPh$_3$)$_4$ (210 mg, 0.179 mmol) in dry THF (10.5 mL) was added. After the mixture was stirred at 20° C. for 10 min, it was warmed to 70° C. for 6 h. The solvent was removed under reduced pressure and the residue was partitioned between water and ether. The layers were separated and the aqueous layer was extracted with ether (3×). The combined organic layers were dried (Na$_2$SO$_4$) and concentrated. The mono-Boc-protected coupling product was purified by column chromatography to give yellow foam (294 mg). A mixture of the yellow foam and TFA (5 mL) was stirred at 20° C. for 1.5 h and concentrated. NH$_4$OH and water were added until the pH of the aqueous layer reached 10–11. The yellow solid formed was collected through filtration and dried under vacuum. The product was purified by column chromatography to give Compound 5 (31 mg, 43%) as a yellow solid. $^1$H NMR (300 MHz, DMSO-d$_6$) δ 10.18 (s, 1H), 8.77 (s, 1H), 8.68 (brs, 1H), 8.15 (s, 1H), 7.75 (s, 1H), 7.68–7.36 (m, 1H), 7.18 (brs, 1H), 6.86 (brd, J=8.1 Hz, 1H), 6.17 (brs, 1H), 4.52 (brs, 1H), 4.24 (s, 4H), 3.53 (m, 2H), 3.15 (m, 2H), 1.75 (m, 2H); MS (ES) m/z: 381 (M+H$^+$). Anal. Calcd. For C$_{19}$H$_{20}$N$_6$O$_3$·0.2H$_2$O: C, 59.43; H, 5.35; N, 21.88. Found: C, 59.47; H, 5.36; N, 21.73.

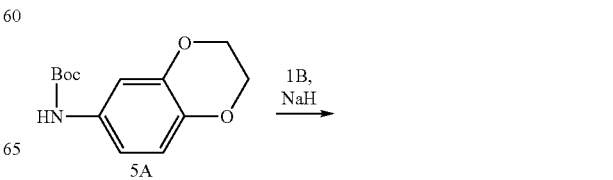

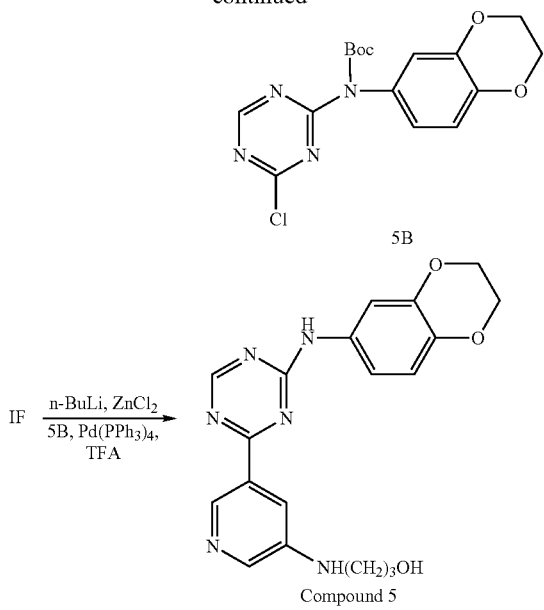

Compound 5

Example 6

3-((5-(4-((4-(4-morpholinyl)phenyl)amino)-1,3,5-triazin-2-yl)-3-pyridinyl)amino)-1-propanol (Compound 6)

4-Morpholinoaniline (5.0 g, 28.0 mmol) was dissolved in THF (50 mL) at 20° C. A THF solution (10 mL) of Boc$_2$O (6.1 g, 28.0 mmol) was added slowly to the mixture of 4-morpholinoaniline and THF and the resulting mixture was stirred for 5 h. After the mixture was concentrated, sonicated in dichloromethane, filtered through celite, the crude product was purified by column chromatography (EtOAc/Hexane) and recrystallization from EtOAc to give Compound 6A (6.05 g, 78%) as a white solid. $^1$H NMR (300 MHz, CDCl$_3$) δ 7.26 (d, J=8.6 Hz, 2H), 6.86 (d, J=8.6 Hz, 2H), 6.31 (brs, 1H), 3.85 (t, J=4.7 Hz, 4H), 3.09 (t, J=4.8 Hz, 4H), 1.50 (s, 9H); MS (ES) m/z: 279 (M+H$^+$). Anal. Calcd. For C$_{15}$H$_{22}$N$_2$O$_3$: C, 64.73; H, 7.97; N, 10.06. Found: C, 64.73; H, 8.01; N, 9.91. THF (50 mL) was added to a mixture of Compound 6A (1.55 mg, 5.57 mmol) and NaH (550 mg, 60% in mineral oil, 13.9 mmol) at 0° C. under nitrogen. After the mixture was stirred at 0° C. for 5 min, it was stirred at 20° C. for 1 h and cooled back to 0° C. Compound 1B (1.0 g, 6.68 mmol) was added and stirred at 20° C. for 20 h. Saturated aqueous NH$_4$Cl was added and the mixture was concentrated. The residue was extracted with EtOAc (3×). The organic extracts were dried (Na$_2$SO$_4$) and concentrated. The product was purified by column chromatography (dichloromethane/acetone) to give Compound 6B (612 mg, 28%) as a solid. $^1$H NMR (300 MHz, CDCl$_3$) δ 8.67 (s, 1H), 7.08 (d, J=6.9 Hz, 2H), 6.93 (d, J=6.9 Hz 2H), 3.87 (t, J=4.8 Hz, 4H), 3.21 (t, J=4.9 Hz, 4H), 1.48 (s, 9H); MS (ES) m/z: 414 (M+Na). Anal. Calcd. For C$_{18}$H$_{22}$N$_5$O$_3$Cl: C, 55.17; H, 5.66; N, 17.87. Found: C, 55.18; H, 5.69; N, 17.73.

n-BuLi (1.47 mL, 2.5 M, 3.61 mmol) was added dropwise to Compound 1F (806 mg, 1.80 mmol) in anhydrous THF (6.4 mL) at −78° C. and stirred for 20 min. Anhydrous zinc chloride (5.4 mL, 1 M in ether, 5.4 mmol) was added dropwise to the mixture of THF and Compound 1F at −78° C. and stirred for 10 min before it was warmed to 20° C. by removing the dry-ice bath. A mixture of Compound 6B (475 mg, 1.2 mmol) and Pd(PPh$_3$)$_4$ (70 mg, 0.06 mmol) in dry THF (5 mL) was added. The resulting mixture was stirred at 20° C. for 10 min and then at 70° C. for 18 h. The solvent was removed under vacuum. The residue was partitioned between water and ether. The layers were separated. The aqueous layer was extracted with ether (3×) and the organic layers were combined, dried (Na$_2$SO$_4$) and concentrated. The mono-Boc-protected coupling product was purified by column chromatography (dichloromethane/acetone) to give yellow foam (105 mg). A mixture of the yellow foam (105 mg), dichloromethane (2 mL) and TFA (0.66 mL) was stirred at 20° C. for 5 h and concentrated. NH$_4$OH and water were added until the pH of the aqueous layer reached 10–11. The yellow solid formed was collected through filtration and dried under vacuum. The product was purified by column chromatography to give Compound 6 (22 mg, 4.5%) as a yellow solid. $^1$H NMR (300 MHz, DMSO-d$_6$) δ 10.13 (s, 1H), 8.75 (s, 1H), 8.68 (brs, 1H), 8.14 (s, 1H), 7.75 (s, 1H), 7.64 (m, 2H), 6.97 (brs, 2H), 6.16 (brs, 1H), 4.53 (t, J=5.0 Hz, 1H), 3.75 (t, J=4.7 Hz, 4H), 3.54 (q, J=6.0 Hz, 2H), 3.19–3.09 (m, 6H), 1.75 (m, 2H); MS (ES) m/z: 408 (M+H$^+$). Anal. Calcd. For C$_{21}$H$_{25}$N$_7$O$_2$.0.6H$_2$O: C, 60.30;H 6.31; N, 23.44. Found: C, 60.19; H, 6.12; N, 23.28.

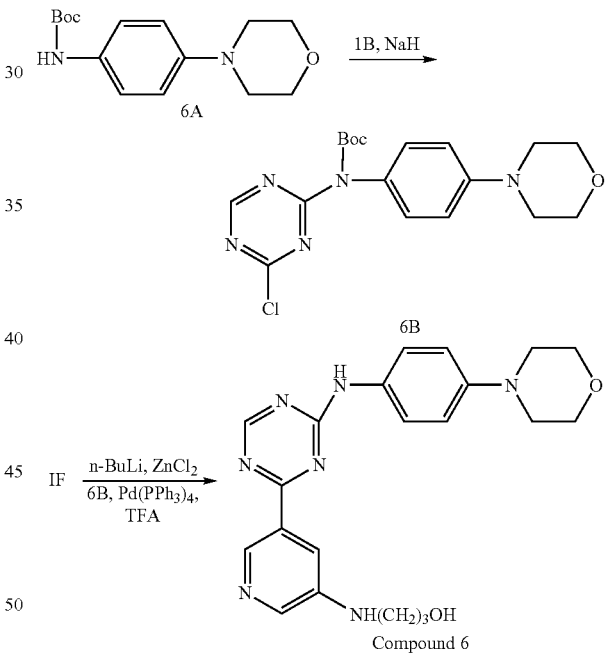

Compound 6

BIOLOGICAL EXAMPLES

The utility of the compounds to treat or ameliorate a kinase mediated disorder was determined using the following procedures.

Example 1

CDK1 Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 μM biotinylated histone-H1 peptide substrate (also referred to herein as a CDK-1 peptide substrate, see substrate table) and 0.2 µCuries per well $^{33}$P-γ-ATP (2000–3000 Ci/mmol). 70 µL of the kinase reaction mixture was dispensed into the well of a streptavidin coated FlashPlate™ (Cat. # SMP 103, NEN, Boston, Mass.). Then 1 µL of test compound stock in 100% DMSO was added to the wells resulting in a final concentration of 1% DMSO in the reaction with a 100 µl final reaction volume. Next, CDK1:Cyclin-B protein (New England Biolads, infra) was diluted in 50 mM Tris-HCl pH=8.0, 0.1% BSA at a concentration of 1 ng per µL and 30 µl (30 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The histone-H1 biotinylated peptide substrate became immobilized on the Flashplate™ (Perkin Elmer, NEN Boston, Mass.) and the incorporation of $^{33}$P-γ-ATP was measured by reading the plate on a scintillation counter. Inhibition of the enzymatic activity of CDK1 was measured by observing a reduced amount of $^{33}$P-γ-ATP incorporated into the immobilized peptide.

VEGF-R Screening Assay

A kinase reaction mixture was prepared containing 50 mM Tris-HCl pH=8, 10 mM MgCl$_2$, 0.1 mM Na$_3$PO$_4$, 1 mM DTT, 10 µM ATP, 0.025 µM biotinylated peptide substrate (also referred to herein as PLC-1 biotinylated peptide substrate and PDGF receptor substrate, sequence provided in the peptide substrate table) and 0.8 µCuries per well $^{33}$P-γ-ATP (2000–3000 Ci/mmol). 70 µL of the kinase reaction mixture was dispensed into the well of a streptavidin coated FlashPlate™ (Cat. # SMP103, NEN, Boston, Mass.). Then 1 µL of test compound stock in 100% DMSO was added to the wells resulting in a final concentration of 1% DMSO in the reaction with a 100 µL final reaction volume. Next, soluble rat VEGF tyrosine kinase containing an N-terminal 6XHIS tag was diluted in 50 mM Tris-HCl pH=8.0, 0.1% BSA at a concentration of 5 ng per µL and 30 µL (150 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The PLC1 biotinylated peptide substrate became immobilized on the Flashplate™ and the incorporation of $^{33}$P-γ-ATP was measured by reading the plate on a scintillation counter. Inhibition of the enzymatic activity of the VEGF-R was measured by observing a reduced amount of $^{33}$P-γ-ATP incorporated into the immobilized peptide.

IC$_{50}$ data for CDK1 and VEGF-R are shown in Table 1. IC$_{50}$ values listed as >10 or >100 indicate no observed 50% inhibition at the highest dose tested, nor was an inhibition maxima observed. ND means not tested.

TABLE 1

| Cpd | CDK1 IC$_{50}$ (µM) | VEGF-R (µM) |
|---|---|---|
| 1 | 0.039 | 2.56 |
| 2 | 0.016 | 2.56 |
| 3 | 0.971 | 12.92 |
| 4 | 0.766 | 0.865 |
| 5 | 0.382 | 10 |
| 6 | 1.24 | 5.03 |

Example 2

Kinase Selectivity Assays

Assays to test compound inhibition of other kinases were preformed using methods that measure the amount of phosphorylation of a biotinylated peptide substrate. Biotinylated peptide substrates were selected from the literature as appropriate for the enzyme being evaluated. The general procedure used to assay for kinase activity is as follows: a kinase reaction mix was prepared in 50 mM Tris-HCl pH=8, 10 mM MgCl$_2$, 0.1 mM Na$_3$VO$_4$, 1 mM DTT, 10 µM ATP, 0.25–1 µM biotinylated peptide substrate, 0.2–0.8 µCuries per well $^{33}$P-γ-ATP (2000–3000 Ci/mmol). Assay conditions vary slightly for each protein kinase, for example, insulin receptor kinase requires 10 mM MnCl$_2$ for activity and Calmodulin-dependent protein kinase requires calmodulin and 2 mM CaCl$_2$. The reaction mixture was dispensed into the wells of a streptavidin coated Flashplate and 1 µL test compound in 100% DMSO was added to a 100 µL reaction volume resulting in a final concentration of 1% DMSO in the reaction. Enzyme was diluted in 50 mM Tris-HCl pH=8.0, 0.1% BSA and added to each well. The reaction was incubated for one hour at 30° C. in the presence of a test compound. After one hour the reaction mix was aspirated from the plate and the plate was washed with PBS containing 100 mM EDTA. The plate was read on a scintillation counter to determine $^{33}$P-γ-ATP incorporated into the immobilized peptide substrate. Test compounds were assayed in duplicate at 8 concentrations (100 µM, 10 µM, 1 µM, 100 nM, 10 nM, 1 nM, 100 pM, 10 pM). A maximum and minimum signal for the assay was determined on each plate. The IC$_{50}$ was calculated from the dose response curve of the percent inhibition of the maximum signal in the assay according to the formula: % Inhibition=((max signal−background)/(test compound signal−background))×(100%), where the percent inhibition was compared to the log concentration of test compound. Known inhibitor compounds appropriate for the kinase being assayed were also included on each plate.

Definition and Source of Kinase Enzymes

The form of VEGF-R (vascular endothelial growth factor receptor-2) used was a fusion protein containing a polyhistidine tag at the N-terminus followed by amino acids 786–1343 of the rat VEGF-R2 kinase domain (GenBank Accession #U93306). The form of CDK1 (cyclin dependent kinase 1) used was isolated from insect cells expressing both the human CDK1 catalytic subunit and its positive regulatory subunit cyclin B (CDK1:cyclin B protein, New England Biolabs, Beverly, Mass., Cat. #6020). The form of CDK4 (cyclin dependent kinase 4) used contains amino acids 769 to 921 of the mouse R6 protein found in the GST-retinoblastoma protein construct (Santa Cruz Biotechnology, Santa Cruz, Calif.; Cat. #SC-4112). The form of EGF-R1 (epidermal growth factor receptor 1) used was purified from human A431 cell membranes (Sigma, St. Louis, Mo., Cat.# E3641). The form of Protein Kinase A used was the catalytic subunit of cAMP dependent protein kinase-A purified from bovine heart (Upstate Biotech, Lake Placid, N.Y., Cat#14–114). The form of PKC (protein kinase-C) used was the γ or β-2 isoform of the human protein produced in insect cells (BIOMOL, Plymouth Meeting, Pa., Cat. #SE-143). The form of Casein Kinase 1 used was a truncation at amino acid 318 of the C-terminal portion of the rat CK1 delta isoform produced in *E. coli* (New England Biolabs, Beverly, Mass., Cat. #6030). The form of Casein Kinase 2 used includes the alpha and beta subunits of the human CK2 protein produced in *E. coli* (New England Biolabs, Beverly, Mass., Cat. #6010). The form of Calmodulin Kinase (calmodulin-dependent protein kinase 2) used was a truncated version of the alpha subunit of the rat protein produced in insect cells (New England Biolabs, Beverly, Mass., Cat. #6060). The form of GSK-3 (Glycogen Synthase Kinase-3) used was the beta isoform of the rabbit enzyme produced in *E. coli* (New England Biolabs, Beverly, Mass., Cat. #6040). The form of MAP Kinase ERK-2 used was the rat ERK-2 isoform containing a polyhistidine tag at the N-terminus produced in *E. coli*. and activated by phosphorylation with MEK1 prior to purification (BIOMOL, Plymouth Meeting, Pa., Cat. #SE-137). The form of Insulin Receptor Kinase used consists of residues 941–1313 of the cytoplasmic domain of the beta-subunit of the human insulin receptor (BIOMOL, Plymouth Meeting, Pa., Cat. #SE-195). The form of PDGF-R (platelet derived growth factor receptor) used was a fusion protein containing a polyhistidine tag at the N-terminus followed by nucleotides 1874–3507 of the human PDGF-R beta subunit kinase domain (Accession #M21616).

Peptide Substrates Listed by Type of Enzyme Assay Listed Below

| | |
|---|---|
| VEGF-R | (Biotin)KHKKLAEGSAYEEV-Amide |
| CDK1 | (Biotin)KTPKKAKKPKTPKKAKKL-Amide |
| CDK4 | GST-Retinoblastoma protein construct (supra) |
| EGF-R1 | (Biotin)DRVYIHPF-Amide |
| Protein Kinase A | (Biotin)GRTGRRNSI-Amide |
| PKC γ | (Biotin)RFARKGSLRQKNV-NH2 |
| PKC β-2 | (Biotin)RFARKGSLRQKNV-NH2 |
| Casein Kinase 1 | (Biotin)KRRRALS(phospho)VASLPGL-Amide |
| Casein Kinase 2 | (Biotin)RREEETEEE-Amide |
| Calmodulin Kinase | (Biotin)KKALRRQETVDAL-Amide |
| GSK-3 | (Biotin)KRREILSRRP(phospho)SYR-Amide |
| MAP Kinase ERK-2 | (Biotin)APRTPGGRR-Amide |
| Insulin Receptor Kinase | (Biotin)TRDIYETDYYRK-Amide |
| PDGF-R | (Biotin)KHKKLAEGSAYEEV-Amide |

The $IC_{50}$ data (in µM) for various kinases is shown in Table 2. $IC_{50}$ values listed as >10 or >100 indicate no observed 50% inhibition at the highest dose tested, nor was an inhibition maxima observed. ND means not tested.

TABLE 2

| Assay | Cpd 1 | Cpd 2 |
|---|---|---|
| VEGF-R | 2.56 | 2.57 |
| CDK1 | 0.039 | 0.016 |
| CDK4 | 1.35 | ND |
| EGF-R1 | >100 | >100 |
| Protein Kinase A | >100 | >100 |
| PKC γ | >100 | ND |
| PKC β-2 | >100 | ND |
| Casein Kinase 1 | 0.115 | 1.41 |
| Casein Kinase 2 | 0.926 | >100 |
| Calmodulin Kinase | 54.2 | >10 |
| GSK-3 | 0.005 | 0.017 |
| MAP Kinase ERK-2 | >100 | >10 |
| Insulin Receptor Kinase | 18.2 | >10 |
| PDGF-R | 1.18 | >100 |

Example 3

Assay to Measure Inhibition of Cell Proliferation

The ability of a test compound to inhibit the proliferation of cell growth was determined by measuring incorporation of $^{14}C$-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), HCT-116 colon carcinoma (CCL-247), MDA-MB-231 (Xenogen Corp.), PC-3 prostate adenocarcinoma (ATCC CRL-1435) and A375 malignant melanoma (ATCC CRL-1619).

Using this method, the effect of a compound on cell growth of cells with many different phenotypes can be determined. Cells were trypsinized and counted and 3000–8000 cells were added to each well of a 96-well CytoStar tissue culture treated scintillating microplate (Amersham #RPNQ0160) in complete medium in a volume of 100 µl. Cells were incubated for 24 hours in complete medium at 37° C. in an atmosphere containing 5% $CO_2$. 1 µL of test compound in 100% DMSO was then added to the wells of the plate. DMSO only was added to control wells. Cells were incubated for 24 more hours in complete medium at 37° C. in an atmosphere containing 5% $CO_2$. Methyl $^{14}C$-thymidine (56 mCi/mmol) (NEN #NEC568 or Amersham #CFA532) was diluted in complete medium and 0.2 µCi/well was added to each well of the CytoStar plate in a volume of 20 µL. The plate was incubated for 24 hours at 37° C. plus 5% $CO_2$ in drug plus $^{14}C$-thymidine. The contents of the plate were discarded into a $^{14}C$ radioactive waste container by inverting the plate and the plate was washed twice with 200 µL PBS. 200 µL of PBS was then added to each well. The top of the plate was sealed with a transparent plate sealer and a white plate backing sealer (Packard #6005199) was applied to the bottom of the plate. The degree of methyl $^{14}C$-thymidine incorporation was quantified on a Packard Top Count.

The $IC_{50}$ data (in µM) for a compound tested in the model of Example 3 is shown in Table 3. ND means not tested.

TABLE 3

Inhibition of cell proliferation $IC_{50}$ (µM)

| Cell line | Cpd 1 | Cpd 2 |
|---|---|---|
| HeLa | 0.298 | 0.105 |
| HCT-116 | 0.278 | 0.048 |
| MDA-MB-231 | 0.330 | ND |
| PC-3 | 0.259 | ND |
| A375 | ND | 0.080 |

Example 4

In Vivo Models—Inhibition of Tumor Growth

The in vivo effect of a compound on the growth of human tumor cells can be evaluated by implanting human tumor cells originating from a variety of different tumor types (such as A375 human melanoma cells) into the hindflank of athymic mice and administering a test compound to the mice.

Animals and Tumor Size

Female nude mice were implanted subcutaneously with 1 mm³ A375 melanoma fragments in the flank. Tumors were monitored twice weekly and then daily as the neoplasms reached the desired size range (about 75 mg). Animals were pairmatched on Day 1 when their tumors were in the 62–144 mg range, and the group mean tumor sizes were 76–77 mg. Estimated tumor weight was calculated using the formula (where w=width and l=length in mm of an A375 melanoma tumor):

$$\text{Tumor Weight (mg)} = \frac{(w^2)(l)}{2}$$

Test Compound Administration

Compound 2 was prepared for i.p. (intraperitoneal) administration in a vehicle containing 1% PEG-2000 in water. Compound 2 was administered (i.p.) at 150, 125 and 100 mg/kg, once a day for 32 consecutive days (qd×32). A no treatment control group (Growth Control group included to discount any effect administration of the PEG vehicle might have on tumor growth), and a PEG vehicle (i.p.; qd to end) control group were included in the test. All treatments were initiated on Day 1 and the study was terminated on Day 57.

Analysis of Results

The tumor growth delay (TGD) method was used in this study. In the TGD method, each animal was euthanized when its A375 neoplasm reached a size of 2.0 g. Mean Day of Survival (MDS) values were calculated for all groups. The treatment-effected mean "increase in survival" of various groups were compared to each other and to the mean survival times of mice receiving vehicle. The MDS values calculated for each group, based on the calculated day of death of each mouse, is given by the formula:

$$\begin{array}{c}\text{Time to Endpoint}\\\text{(Calculated)}\end{array} = \begin{array}{c}\text{Time to Exceed}\\\text{Endpoint}\\\text{(Observed)}\end{array} - \left[\frac{Wt_2 - \text{Endpoint Weight}}{\frac{Wt_2 - Wt_1}{D_2 - D_1}}\right]$$

Time to exceed endpoint (observed)=number of days it takes for each tumor to grow past the endpoint (cut-off) size. Once the tumor reaches the cut-off size, the animal is euthanized.

$D_2$=day animal is euthanized.
$D_1$=last day of caliper measurement before tumor reaches the endpoint.
$Wt_2$=tumor weight (mg) on $D_2$
$Wt_1$=tumor weight (mg) on $D_1$
Endpoint weight=predetermined "cut-off" tumor size for the model being used.

Animals were weighed twice weekly during the study. Mice were examined frequently for clinical signs of any adverse, drug-related side effects. Acceptable toxicity for cancer drugs in mice is defined by the NCI as no mean group weight loss of over 20% during the test, and not more than one toxic death among ten treated animals.

Discussion of Results

As shown in Table 4, Compound 2 had approximately equivalent efficacy at the two oral treatment (qd to end) high doses of 150 and 125 mg/kg against the A375 melanoma xenograft.

The 150 mg/kg dose group of six mice had an MDS value of 33.6 days, surviving about 12 days longer than the mice in the PEG vehicle control and Growth Control groups (a survival increase of about 55%). One out of six animals treated at the 150 mg/kg dose survived at day 57.

The 125 mg/kg dose group of six mice had an MDS value of 35.2 days, surviving about 14 days longer than the mice in the PEG vehicle control and Growth Control groups (a survival increase of about 63%). One out of six animals treated at the 125 mg/kg dose survived at day 57.

The 150 and 125 mg/kg dose groups satisfied the NCI definition for acceptable toxicity of a cancer drug in mice, with no mean group weight loss of over 20% during the test and not more than one toxic death among ten treated animals.

The 100 mg/kg dose group of six mice had an MDS value of 29.6 days, surviving about 8 days longer than the mice in the PEG vehicle control and Growth Control groups (a survival increase of about 37%). None of the animals treated at the 100 mg/kg dose survived at day 57.

TABLE 4

Treatment Response Summary

| Group | n | Agent | mg/kg | MDS to 2.0 g ± SEM (n) | Max % BW loss (day) |
|---|---|---|---|---|---|
| 1 | 10 | Growth Control | — | 21.4 ± 2.5 (9) | −13.4% (19) |
| 2 | 10 | 1% PEG 2000 Veh | — | 21.7 ± 2.2 (10) | −11.7% (22) |
| 3 | 6 | Cpd 2 | 150 | 33.6 ± 3.0 (4) | −17.6% (33) |
| 4 | 6 | Cpd 2 | 125 | 35.2 ± 3.6 (5) | −18.8% (29) |
| 5 | 6 | Cpd 2 | 100 | 29.6 ± 3.1 (6) | −17.2% (33) |

While the foregoing specification teaches the principles of the present invention, with examples provided for the purpose of illustration, it will be understood that the practice of the invention encompasses all of the usual variations, adaptations and modifications as come within the scope of the following claims and their equivalents.

The references cited here are incorporated by reference in their entirety.

What is claimed is:

1. A compound of Formula (I):

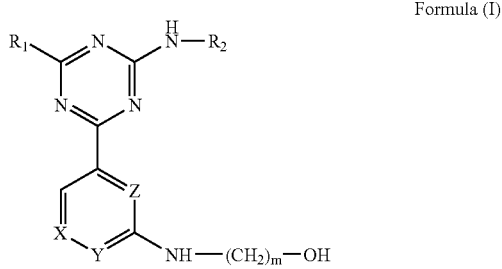

Formula (I)

wherein

X, Y and Z are independently selected from the group consisting of CH and N;

wherein m is an integer from 2 to 5; wherein X, Y and Z include at least one CH atom and at least one N atom; and, wherein a N atom may simultaneously occupy only the X and Z positions;

$R_1$ is selected from the group consisting of hydrogen and $NH_2$; and, $R_2$ is selected from the group consisting of phenyl, wherein phenyl is substituted with one substituent selected from the group consisting of halogen and heterocyclyl, and 1,4-benzodioxinyl;

or a pharmaceutically acceptable salt thereof.

2. The compound of claim 1 wherein X, Y and Z are independently selected from the group consisting of CH and N; wherein m is 3; wherein X, Y and Z include at least one CH atom and at least one N atom; wherein a N atom may simultaneously occupy only the X and Z positions; wherein the heteroaryl ring thus formed is selected from the group consisting of pyridinyl and pyrazinyl; wherein pyridinyl is attached to the triazine ring at the 3 or 4 position of the pyridine ring; and, wherein pyrazinyl is attached to the triazine ring at the 6 position of the pyrazine ring.

3. The compound of claim 1 wherein $R_2$ is selected from the group consisting of phenyl (wherein phenyl is substituted with one substituent selected from the group consisting of chlorine and 4-morpholinyl) and 1,4-benzodioxinyl.

4. The compound of claim 1 wherein the compound of Formula (I) is selected from a compound wherein m is 3; and, wherein X, Y, Z, $R_1$ and $R_2$ are dependently selected from:

| X | Y | Z | $R_1$ | $R_2$ |
|---|---|---|---|---|
| N | CH | CH | H | 3-Cl—Ph; |
| CH | N | CH | H | 3-Cl—Ph; |
| N | CH | N | H | 3-Cl—Ph; |
| CH | N | CH | $NH_2$ | 3-Cl—Ph; |
| N | CH | CH | H | 2,3-dihydro-1,4-benzodioxin-6-yl; or, |
| N | CH | CH | H | 4-(4-morpholinyl)Ph. |

5. A composition comprising a compound of claim 1 and a pharmaceutically appropriate carrier.

6. A method for preparing a composition comprising mixing a compound of claim 1 and a pharmaceutically appropriate carrier.

7. A method for treating human melanoma in a subject in need thereof comprising administering to the subject a therapeutically effective amount of a compound of Formula (I):

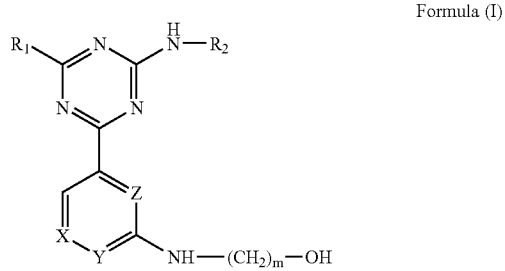

Formula (I)

wherein

X, Y and Z are independently selected from the group consisting of CH and N;

wherein m is an integer from 2 to 5; wherein X, Y and Z include at least one CH atom and at least one N atom; and, wherein a N atom may simultaneously occupy only the X and Z positions;

R1 is selected from the group consisting of hydrogen and NH2; and,

R2 is selected from the group consisting of phenyl, (wherein phenyl is substituted with one substituent selected from the group consisting of halogen and heterocyclyl), and 1,4-benzodioxinyl;

or a pharmaceutically acceptable salt thereof.

8. The method of claim 7 wherein the therapeutically effective amount is from about 0.001 mg/kg/day to about 300 mg/kg/day.

9. A method for treating rheumatoid arthritis in a subject in need thereof comprising administering to the subject a therapeutically effective amount of a compound of Formula (I):

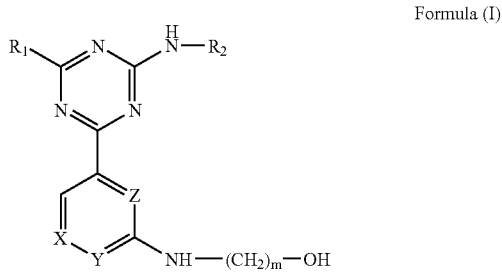

Formula (I)

wherein

X, Y and Z are independently selected from the group consisting of CH and N;

wherein m is an integer from 2 to 5; wherein X, Y and Z include at least one CH atom and at least one N atom; and, wherein a N atom may simultaneously occupy only the X and Z positions;

R1 is selected from the group consisting of hydrogen and NH2; and,

R2 is selected from the group consisting of phenyl, (wherein phenyl is substituted with one substituent selected from the group consisting of halogen and heterocyclyl), and 1,4-benzodioxinyl;

or a pharmaceutically acceptable salt thereof.

10. The method of claim 9 wherein the therapeutically effective amount is from about 0.00 1 mg/kg/day to about 300 mg/kg/day.

* * * * *